(12) United States Patent
Devalaraja et al.

(10) Patent No.: US 7,108,852 B2
(45) Date of Patent: Sep. 19, 2006

(54) METHODS OF TREATING INFLAMMATION USING ANTIBODIES TO M-CSF

(75) Inventors: Madhav N. Devalaraja, Ann Arbor, MI (US); Joseph E. Low, Ann Arbor, MI (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/885,259

(22) Filed: Feb. 23, 2001

(65) Prior Publication Data

US 2002/0141994 A1    Oct. 3, 2002

Related U.S. Application Data

(60) Provisional application No. 60/190,842, filed on Mar. 20, 2000.

(51) Int. Cl.
*A61K 39/395*    (2006.01)
*A61K 39/00*    (2006.01)

(52) U.S. Cl. .............................. 424/130.1; 424/184.1; 424/141.7

(58) Field of Classification Search ............. 424/130.1, 424/184.1, 141.1
See application file for complete search history.

(56) References Cited

U.S. PATENT DOCUMENTS

| | | | |
|---|---|---|---|
| 4,504,586 A | | 3/1985 | Nicholson et al. |
| 4,847,201 A | | 7/1989 | Kaswasaki et al. |
| 4,868,119 A | | 9/1989 | Clark et al. |
| 4,929,700 A | | 5/1990 | Halenbeck et al. |
| 5,470,569 A | | 11/1995 | Kawasaki et al. |
| 5,470,578 A | * | 11/1995 | Aoki et al. |
| 5,491,065 A | | 2/1996 | Halenbeck et al. |
| 5,573,763 A | | 11/1996 | Clark et al. |
| 5,643,563 A | | 7/1997 | Ladner et al. |
| 5,681,719 A | | 10/1997 | Ladner et al. |
| 5,792,450 A | | 8/1998 | Wilson et al. |
| 5,837,229 A | | 11/1998 | Ralph et al. |
| 5,837,460 A | * | 11/1998 | Von Feldt et al. ............. 435/6 |
| 6,103,224 A | | 8/2000 | Ladner et al. |
| 6,117,422 A | | 9/2000 | Ladner et al. |
| 6,146,851 A | | 11/2000 | Ladner et al. |
| 6,204,020 B1 | | 3/2001 | Ladner et al. |
| 6,322,779 B1 | | 11/2001 | Halenbeck et al. |

FOREIGN PATENT DOCUMENTS

| | | | |
|---|---|---|---|
| WO | WO 91/08774 | | 6/1991 |
| WO | WO00/09561 | * | 2/2000 |
| WO | WO 2004/045532 | | 6/2004 |

OTHER PUBLICATIONS

Van Noort et al. International Review of Cytology, 1998.*
Mikayama et al. PNAS, 1993. 90: 10056-10060.*
Ngo et al, iThe Protein Folding Problem and Tertiary Structure Prediction, 1994. (ed.), Birkhauser, Boston, MA, pp. 433 and 492-495.*
Mestas et al J. of Immunology, 2004, 172, pp. 2731-2738.*
Janeway et al. Immunobiology, Third Edition, 1999, pp. 650-651.*
Bischof, R.J.,et al., Clin Exp Immunol 2000; 119: pp. 361-367.
Cook, A. D. et al., Arthritis Res 2001, 3: pp. 293-298.
Campbell, I. K et al., The Journal of Immunology, 1998, V 161 pp. 3639-3644.
Verdrengh M. and Tarkowski A., Infection and Immunity, Feb. 1998. pp. 853-855.
McQualter, J. L., J. Exp. Med, vol. 194, No. 7, Oct. 1, 2001, pp. 873-881.
Aharinejad, S. Cancer Research 62, Sep. 15, 2002, pp. 5317-5324.
Campbell, I. K., Journal of Leukocyte Biology, vol. 68, Jul. 2000, pp. 144-150.
M. Feldman et al., "Anti-TNF α Therapy is Useful in Rheumatoid Arthritis and Crohn's Disease: Analysis of the Mechanism of Action Predicts Utility in Other Diseases", Transplantation Proceedings 1998, 30:4126-4127.
R.O. Williams et al., "Anti-Tumor Necrosis Factor Ameliorates Joint Disease in Murine Collagen-Induced Arthritis", Proc. Natl. Acad. Sci. USA Immunology 1992, 89:9784-9788.
Handschumacher (1990), Drugs Used for Immunosuppression , pp. 1264-1276, in Goodman and Gilman's The Pharmacological Basis of Therapeutics, 8th Edition, Gilman et al. (eds.), Pergamon Press, New York.
Terato, Kuniaki, et al, "Collagen-Induced Arthritis in Mice: Synergistic Effect of *E. Coli* Lipopolysaccharide Bypasses Epitope Specificity in the Induction of Arthritis with Monoclonal Antibodies to Type II Collagen", Autoimmunity, 1995, vol. 22, pp. 137-147.
Terato, Kuniaki, et al, "Induction of Arthritis with Monoclonal Antibodies to Collagen", Journal of Immunilogy, vol. 148, No. 7, 1992, pp. 2103-2108.
Abstract of JP 05095794.
Abstract of JP 06194367.
Abstract of JP 06319584.
Metcalf, D., The molecular control of cell division, differentiation commitment and maturation in haemopoietic cells, Nature, May 4, 1989, vol. 339, 27-30.

* cited by examiner

*Primary Examiner*—Christina Chan
*Assistant Examiner*—Michail A. Belyavskyi
(74) *Attorney, Agent, or Firm*—Charles W. Ashbrook; Todd M. Crissey; Eric J. Baude

(57)    ABSTRACT

A hematopoetic factor called "colony stimulating factor" (CSF) is capable of synergizing the attracting capabilities of chemokines and of inducing the accumulation and/or activation in vitro and in vivo of key components of inflammatory responses. Various types of agents that inhibit or otherwise hinder the production, release or activity of CSF could be used therapeutically in the treatment of ischemia and other inflammatory diseases, such as autoimmune disease, and various chronic inflammatory diseases such as rheumatoid arthritis and psoriasis.

7 Claims, 21 Drawing Sheets

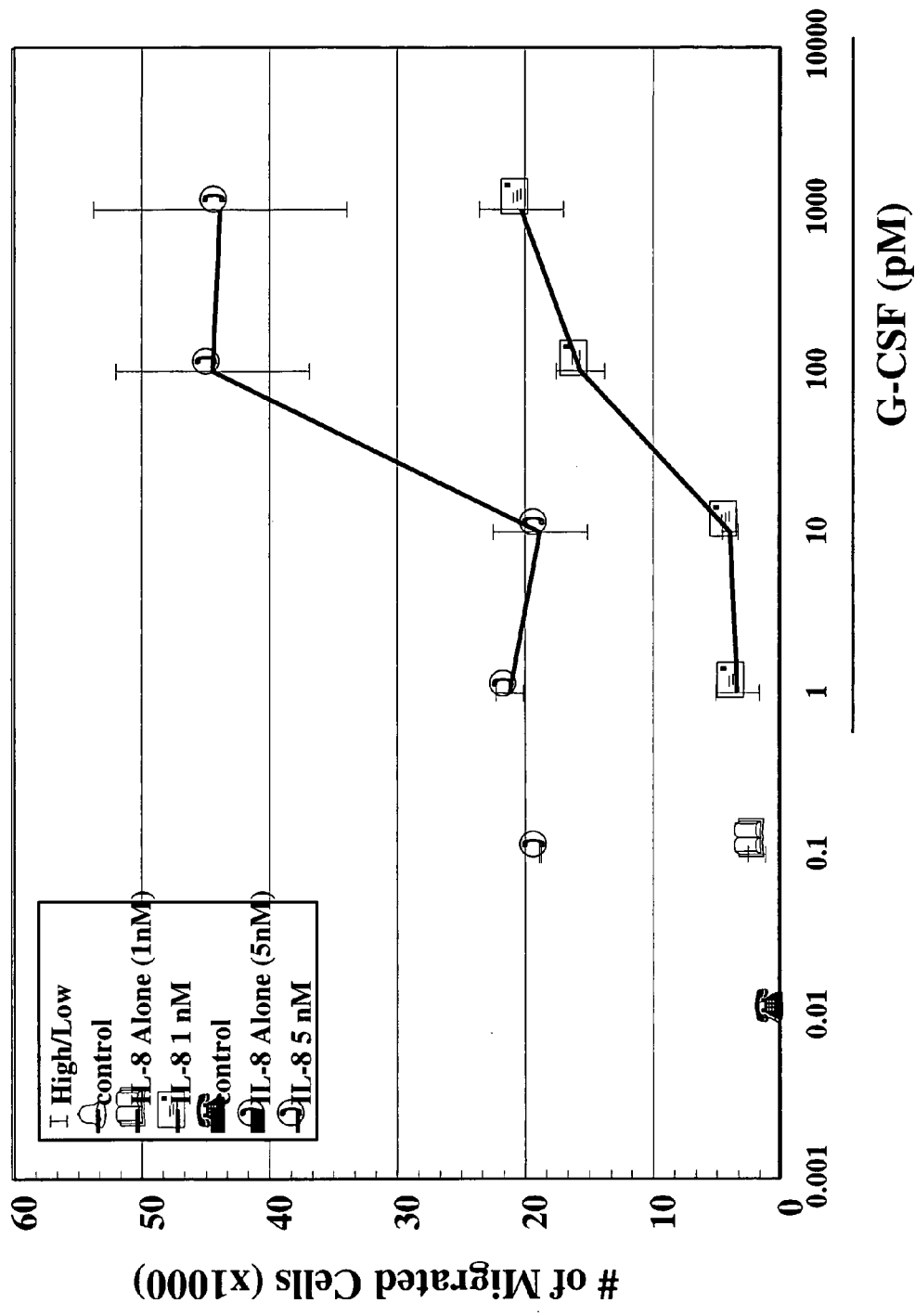
Fig. 1. G-CSF Synergizes IL-8 Induced Neutrophil Chemotaxis

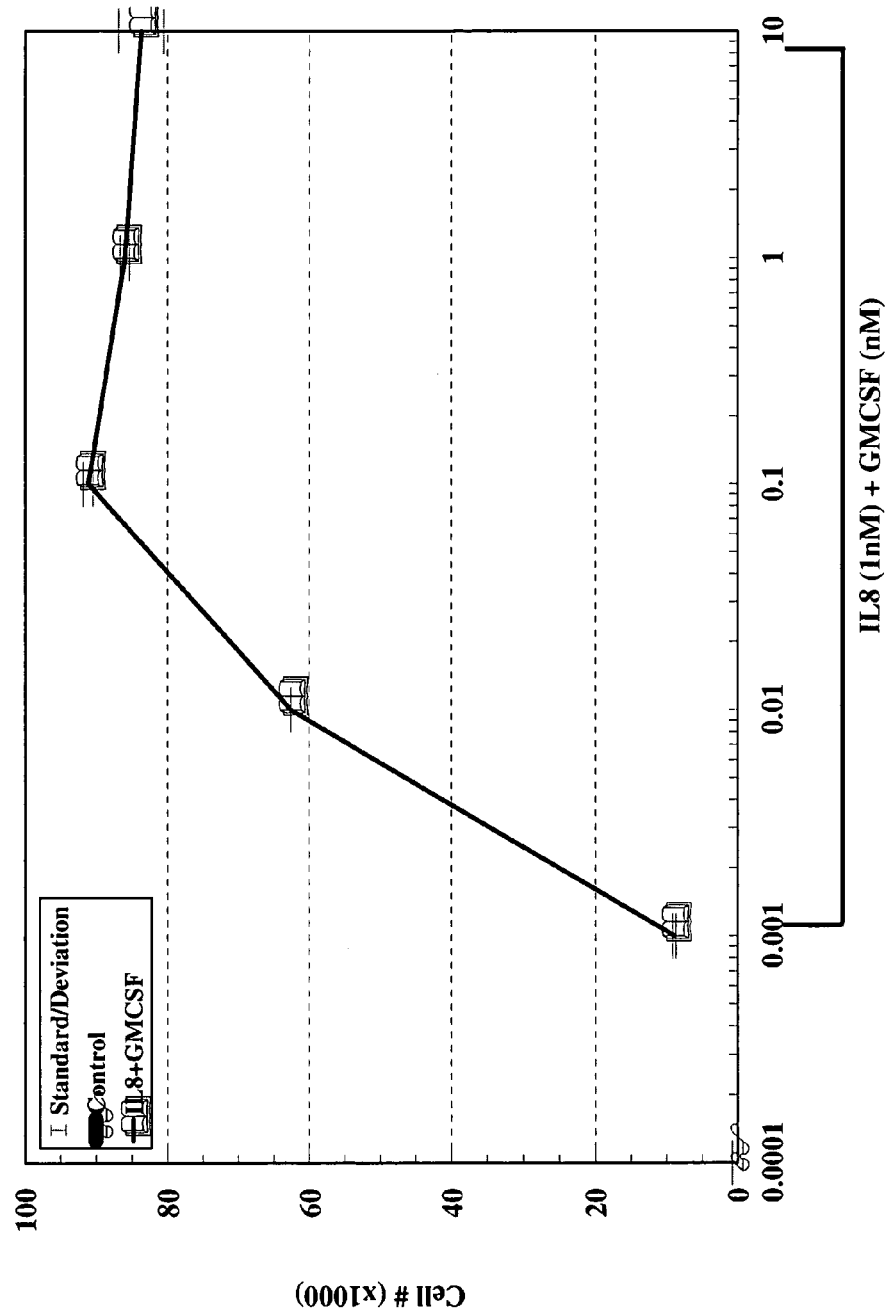

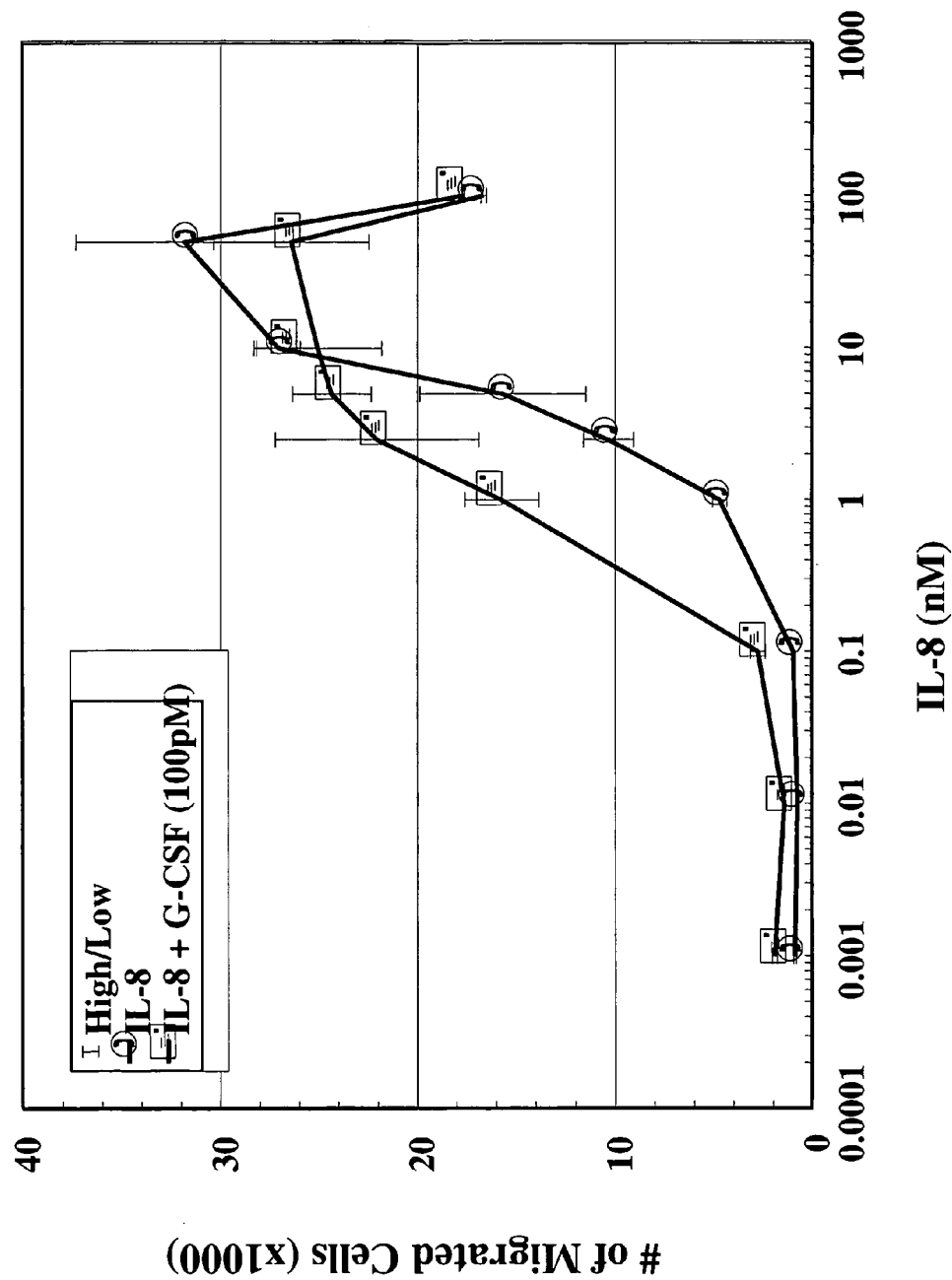
Fig. 3. Dose Response Curve for IL-8 with Constant G-CSF (100 pM)

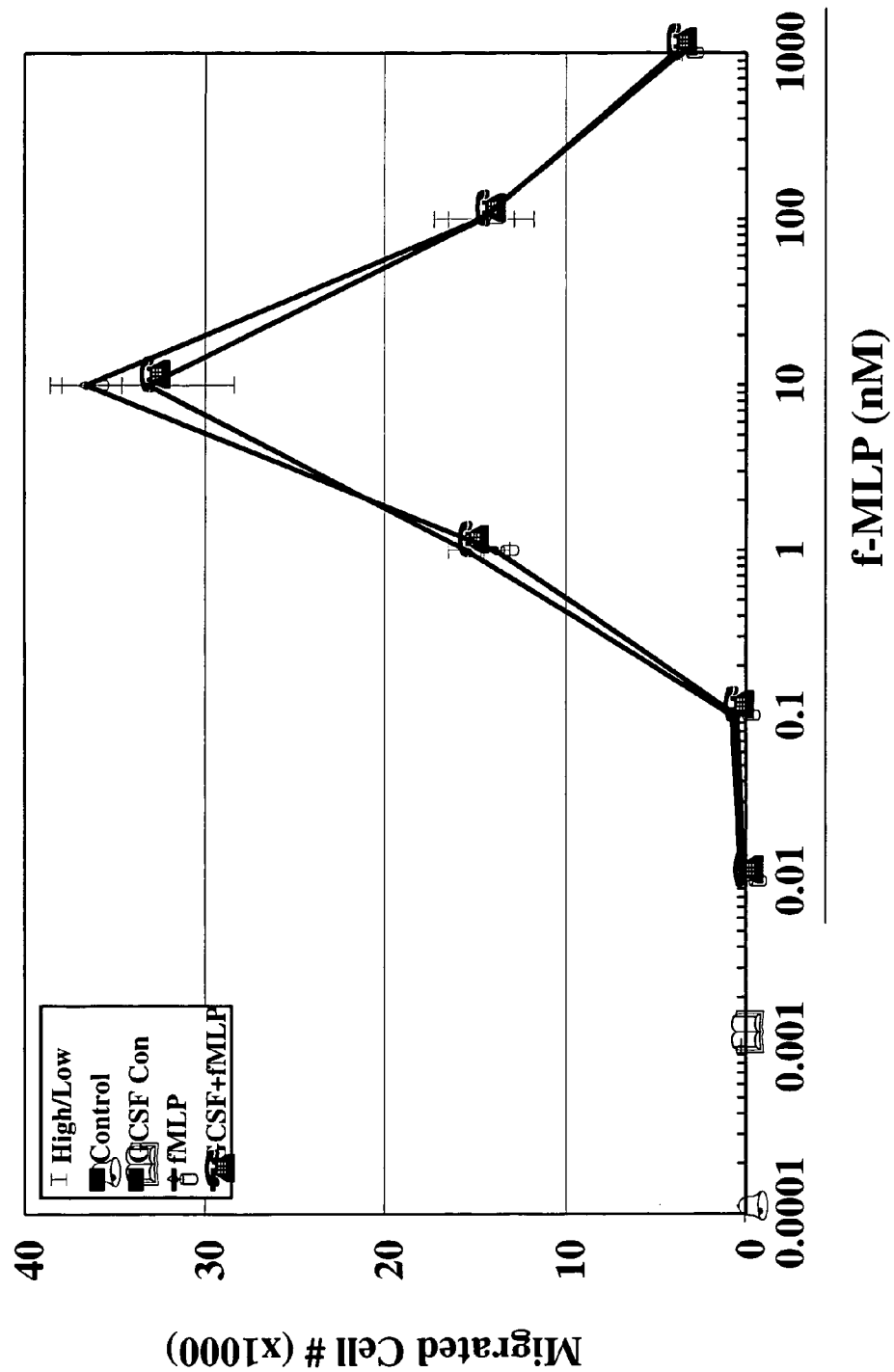

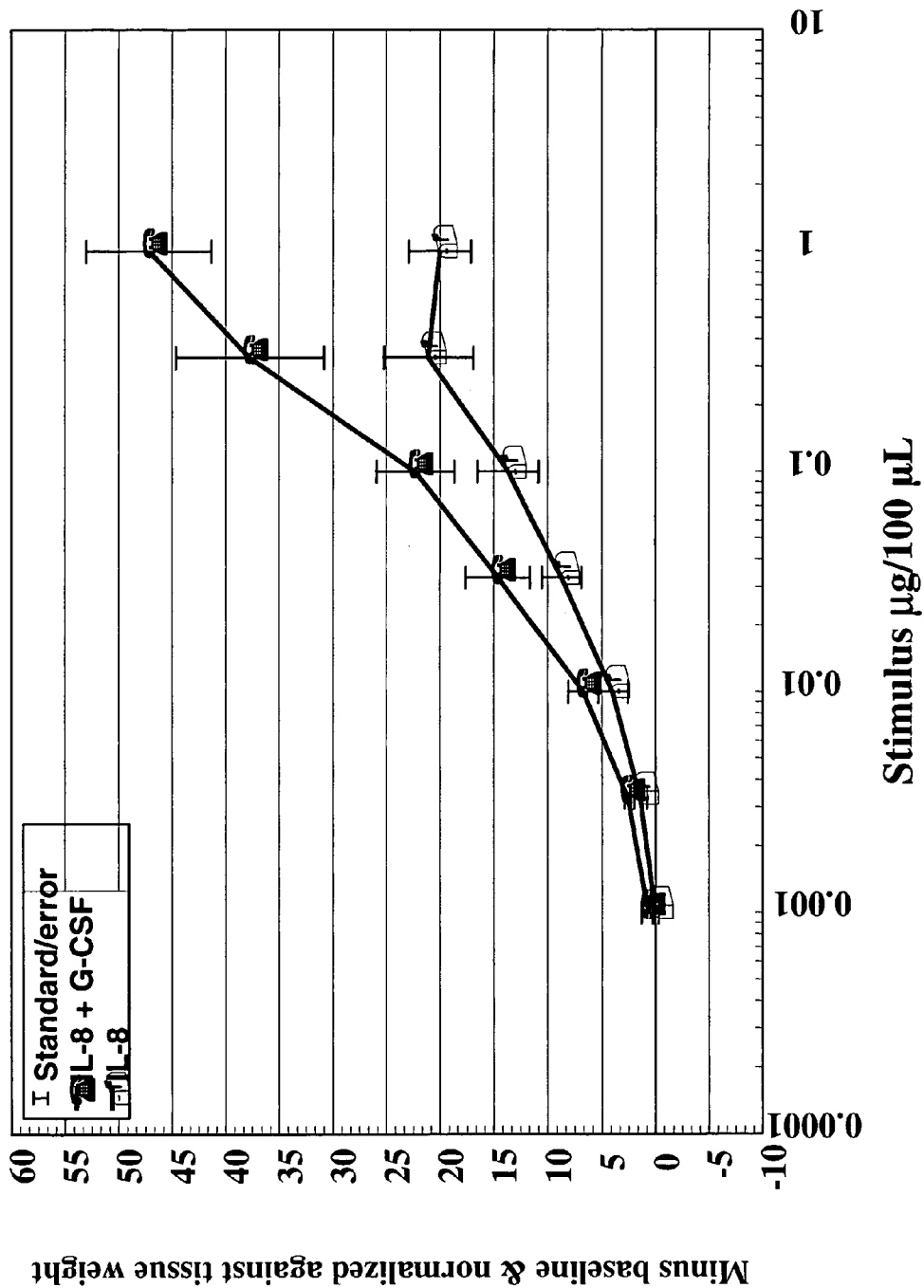
Fig. 5. G-CSF enhances *in vivo* neutrophil intradermal recruitment

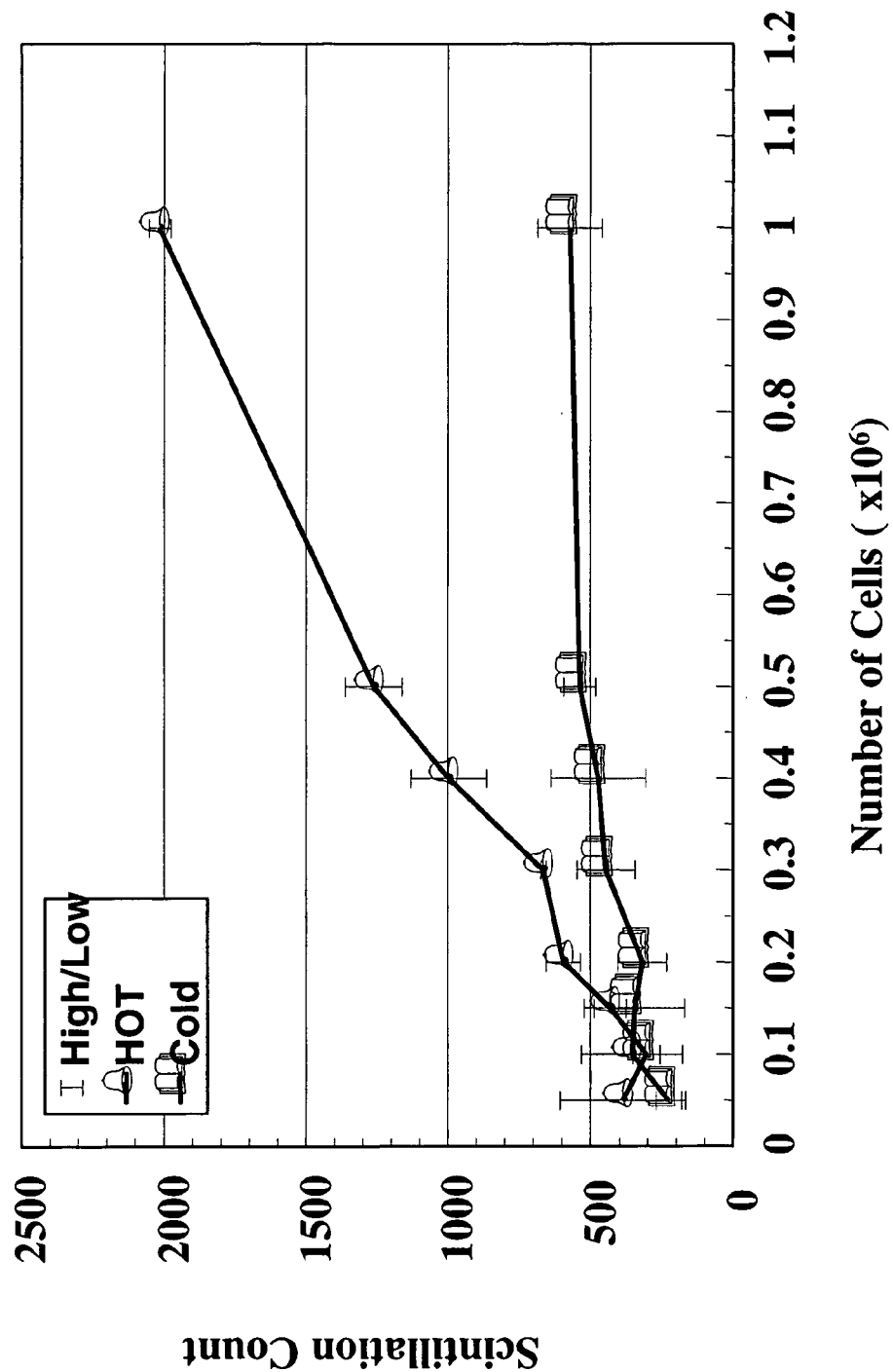
Fig. 6. Binding of $^{125}$I G-CSF on PMN

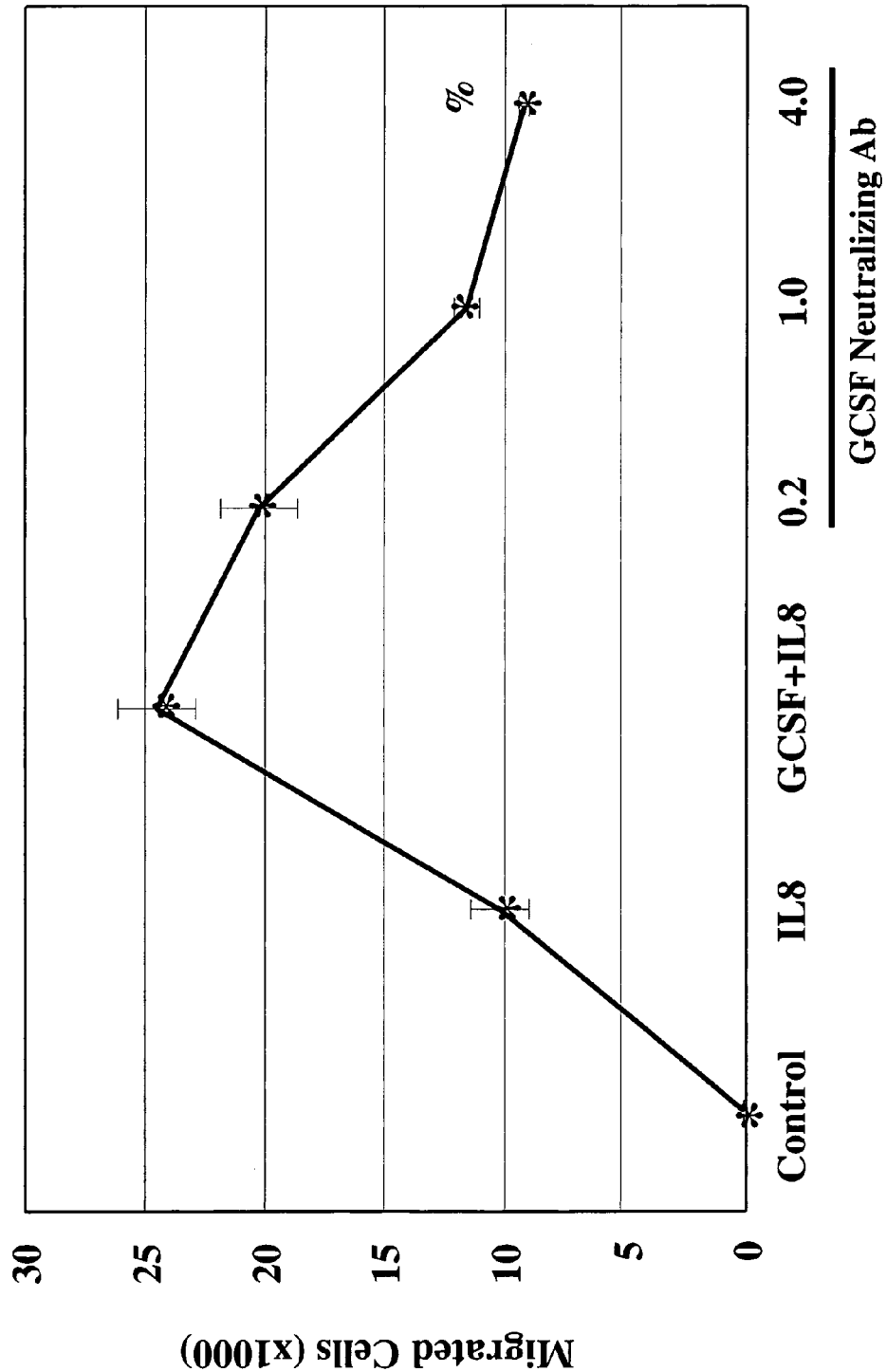
Fig. 7. G-CSF Neutralizing Antibody Inhibits G-CSF Synergized Chemotaxis

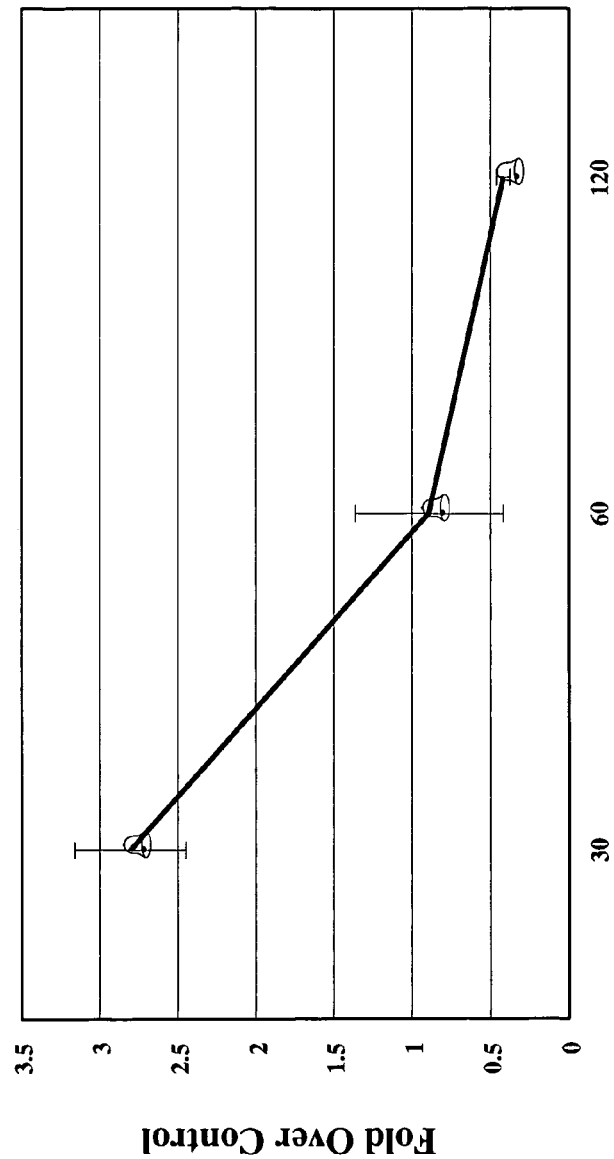
Fig. 8. G-CSF Pre-Incubation Decreases Neutrophil Response to IL-8
Cells were preincubated with G-CSF for respective time periods and subsequently treated with 1nM of IL-8

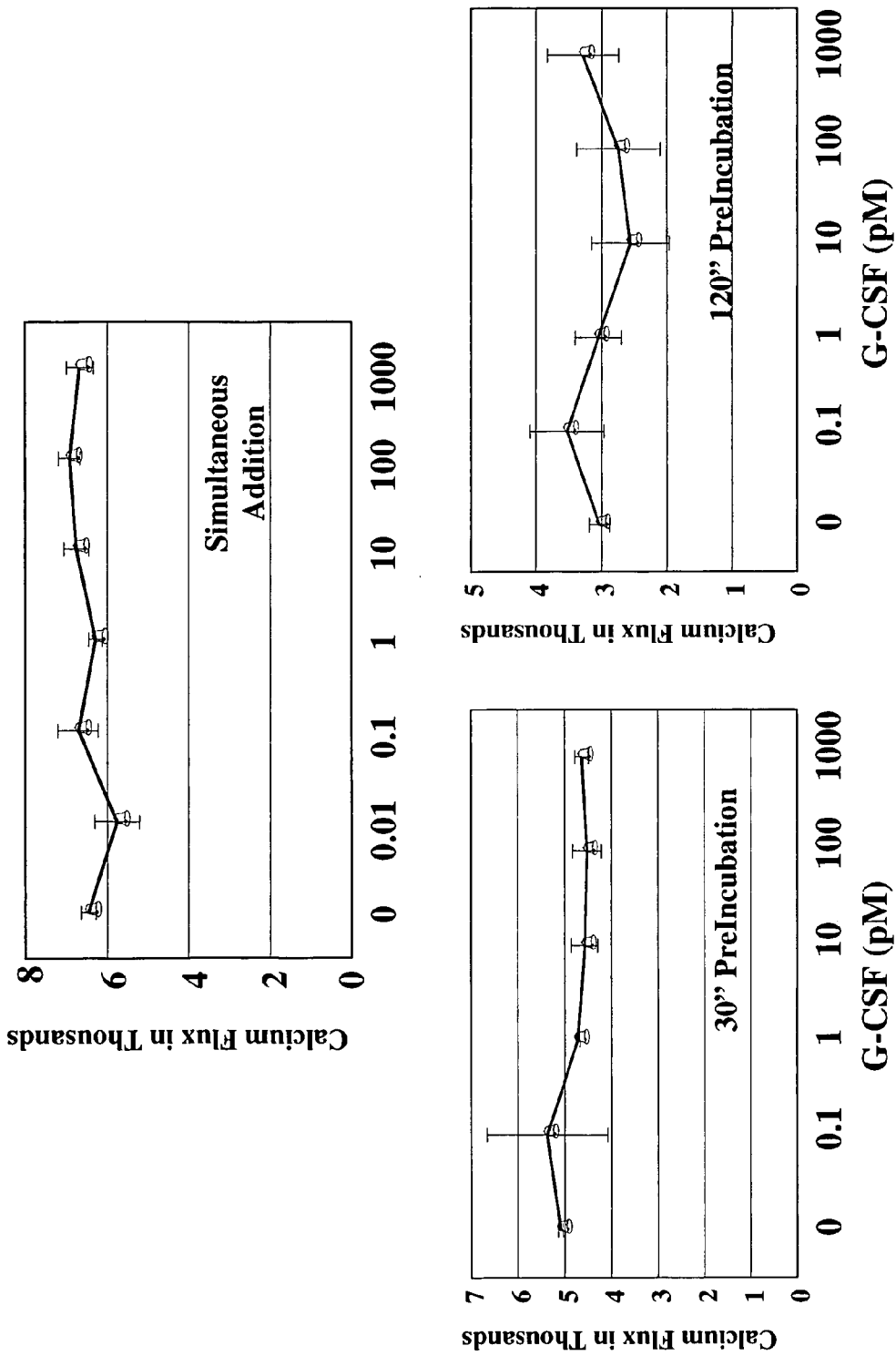
Fig. 9. G-CSF Does not Alter IL-8 Induced Calcium Flux

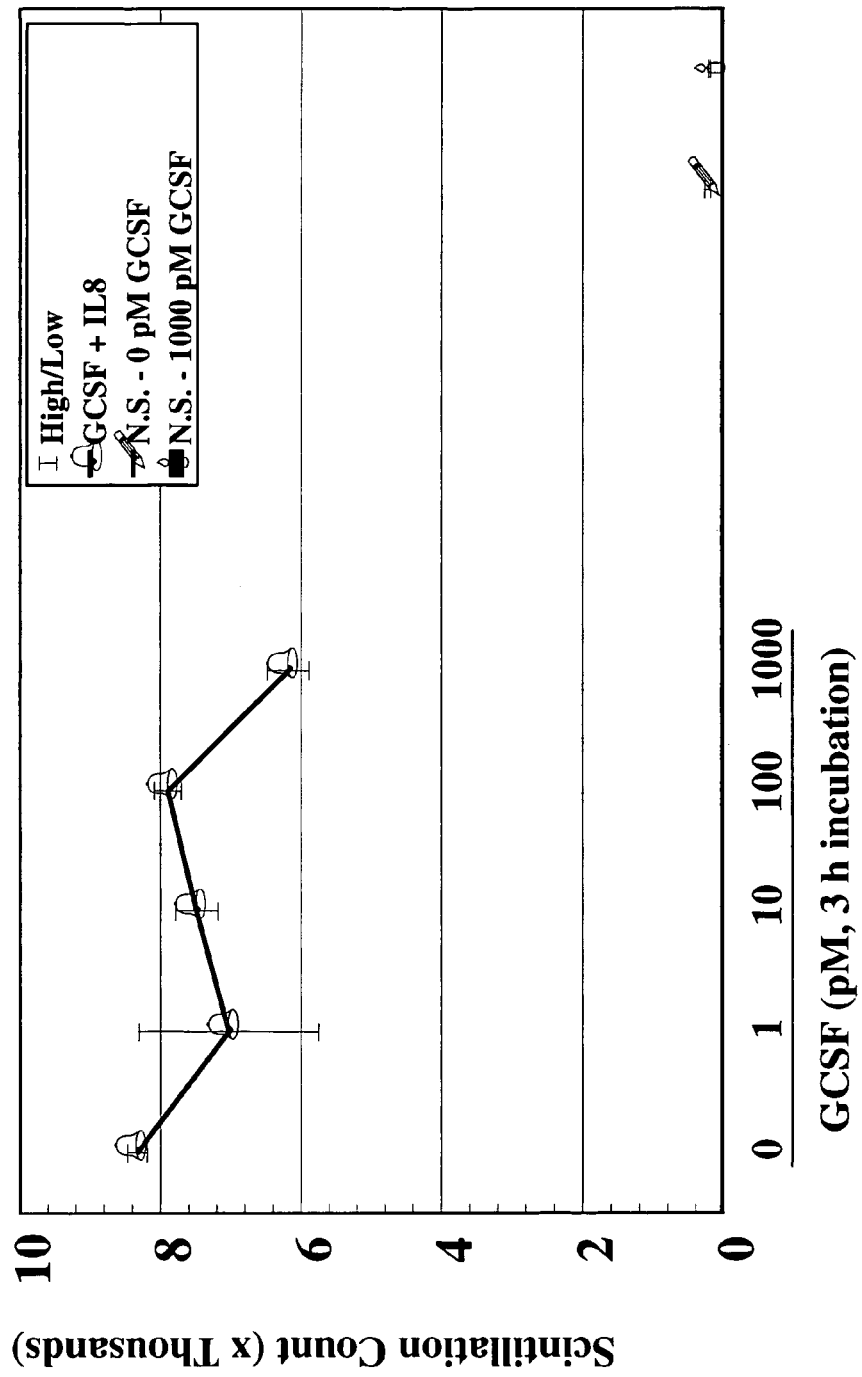
Fig. 10. G-CSF Does Not Increase IL-8 Binding in Neutrophils

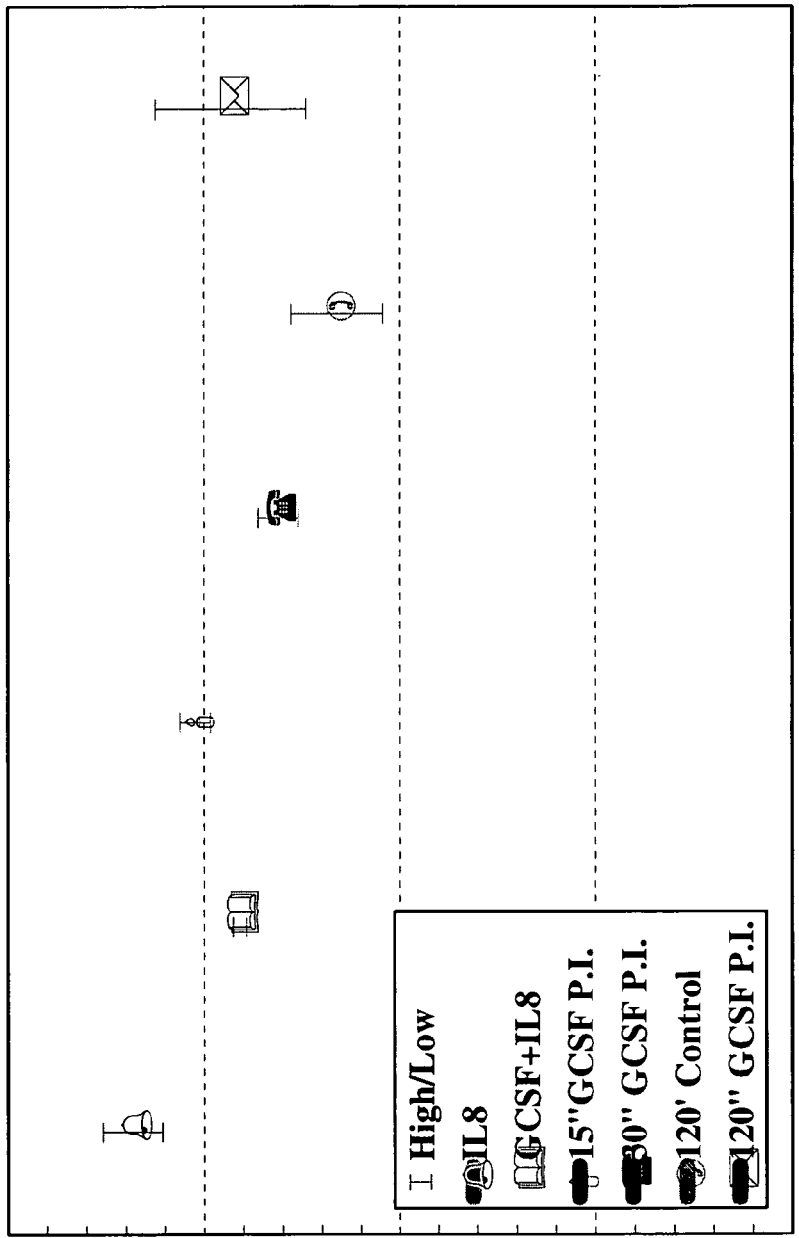
Fig. 11. G-CSF Preincubation Does not Alter IL-8 Binding on Neutrophils
100 pM of G-CSF was incubated simultaneously or pretreated for the respective time periods

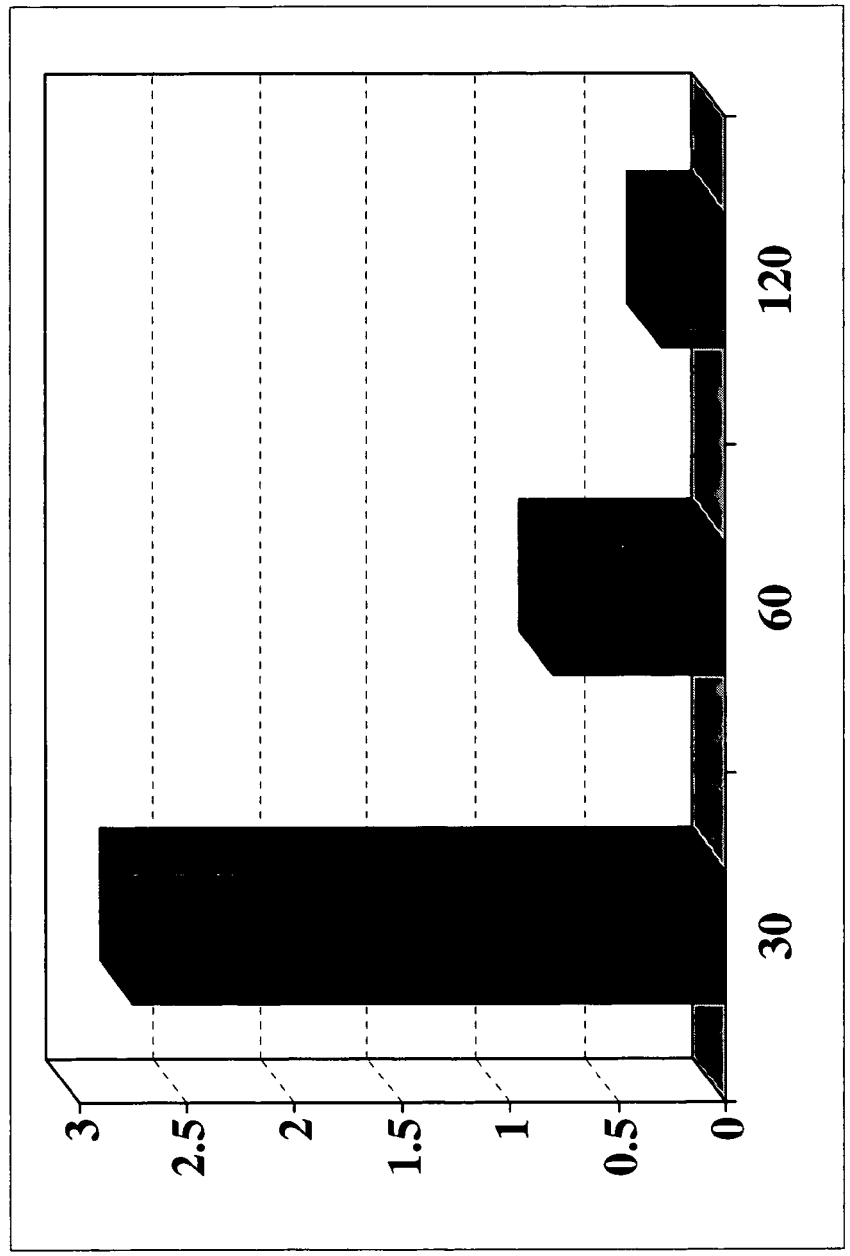
Fig. 12 G-CSF Pre-Incubation Alters PMN Response to LI-8

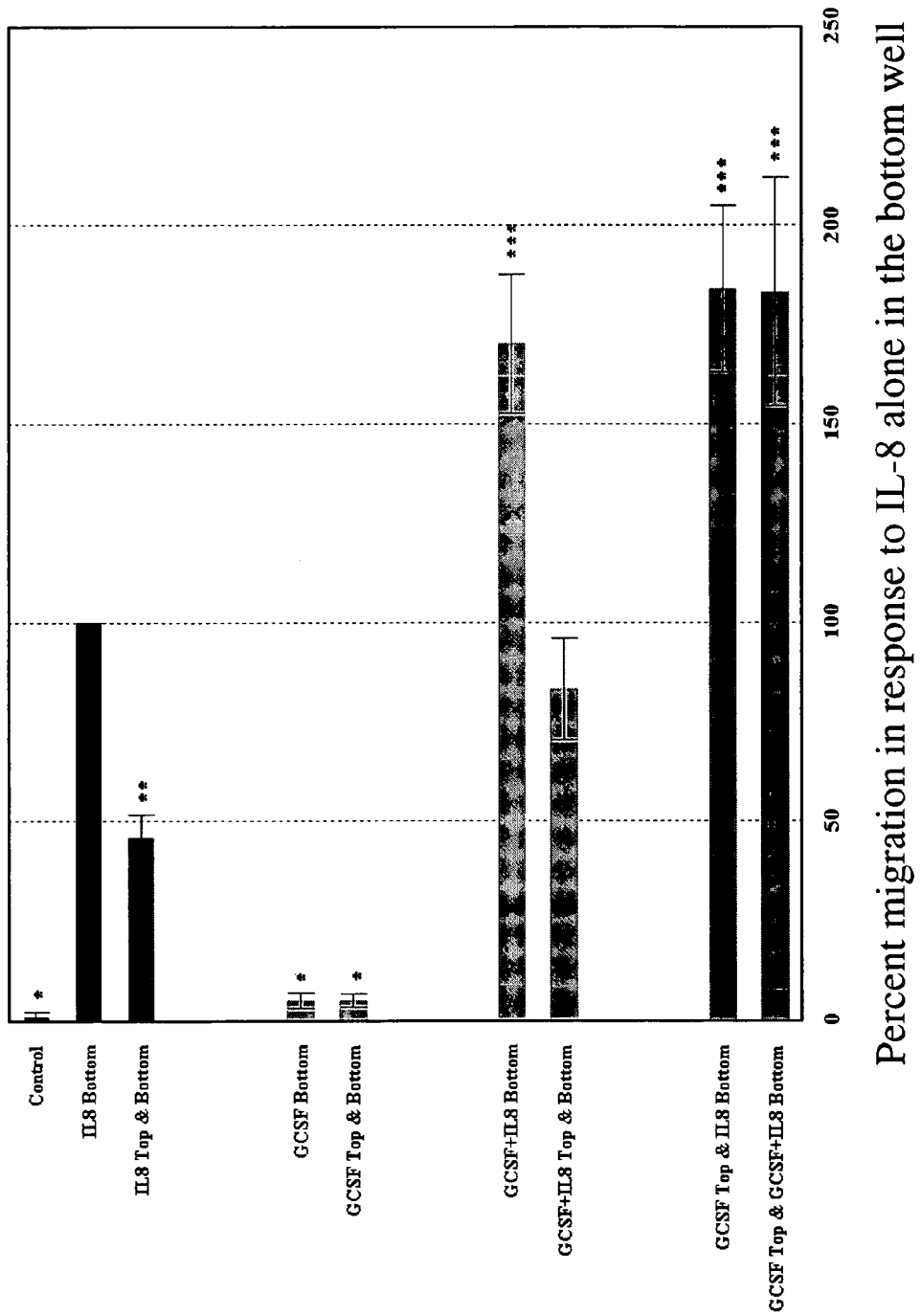
Figure 13: G-CSF potentiates both chemokinetic and chemotactic effects of IL-8

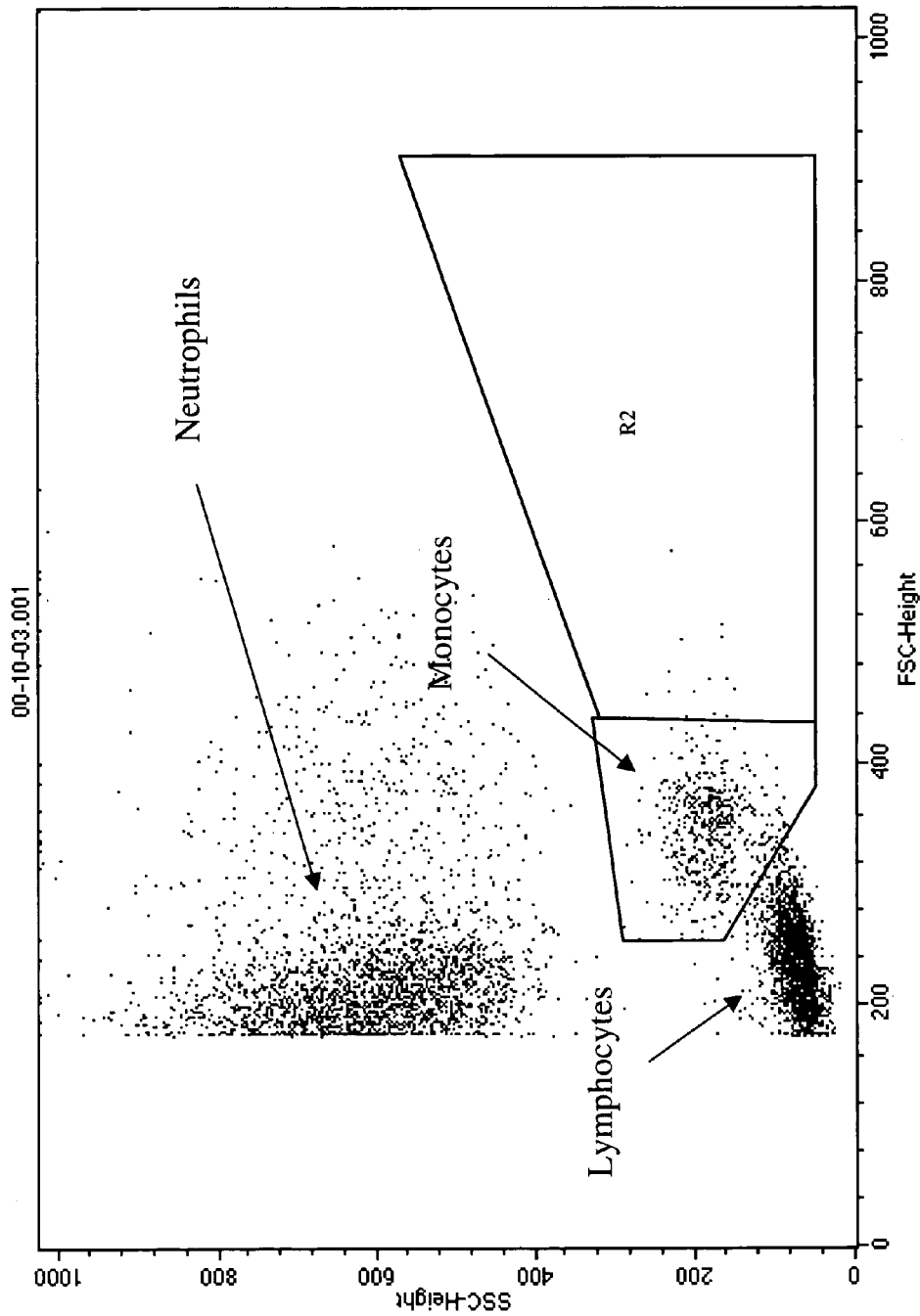
Figure 14: FACS Dot plot of FSC vs. SSC from unstimulated human whole blood

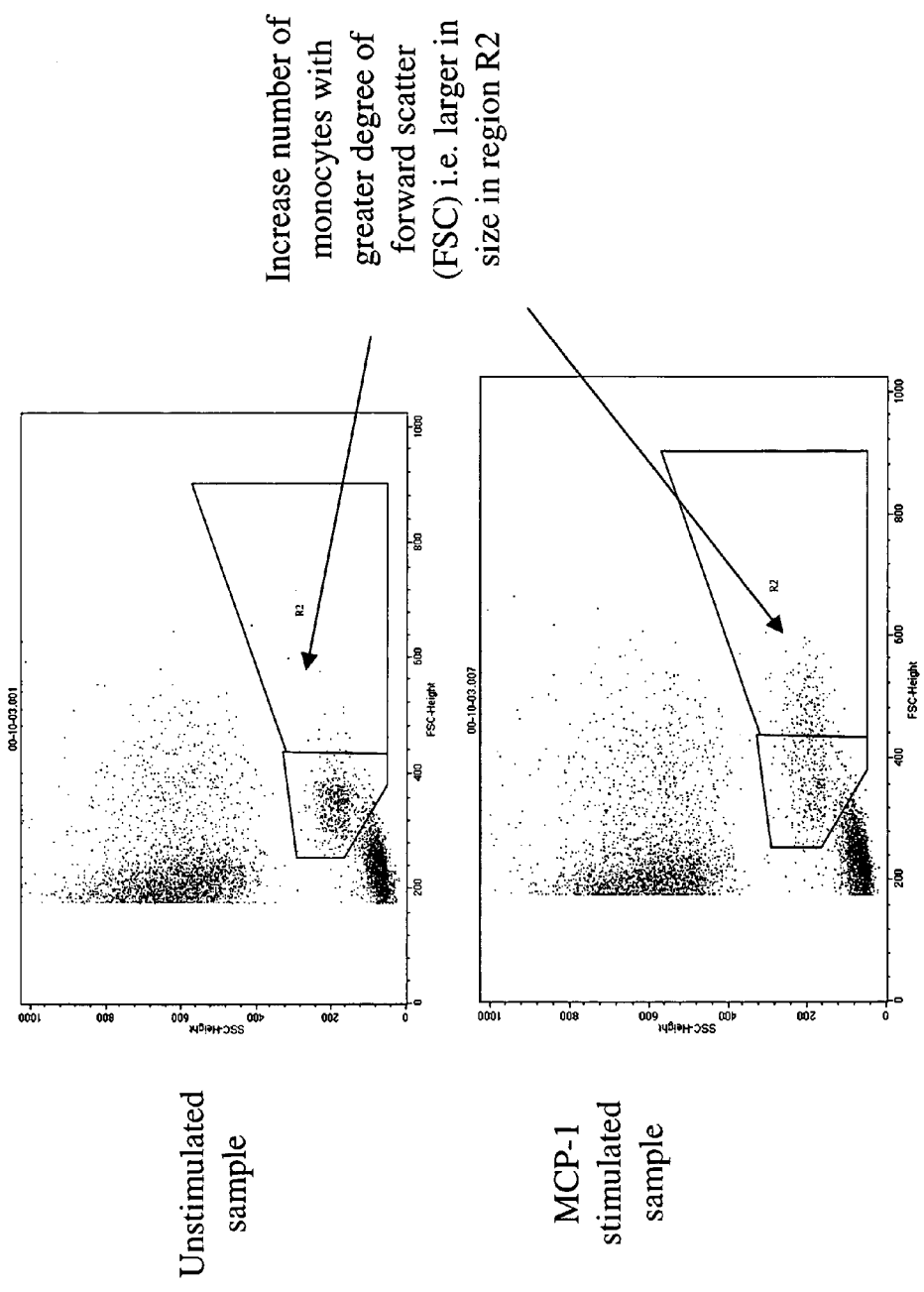
Figure 15: FACS Dot plot of FSC vs. SSC from unstimulated and MCP-1 stimulated human whole blood

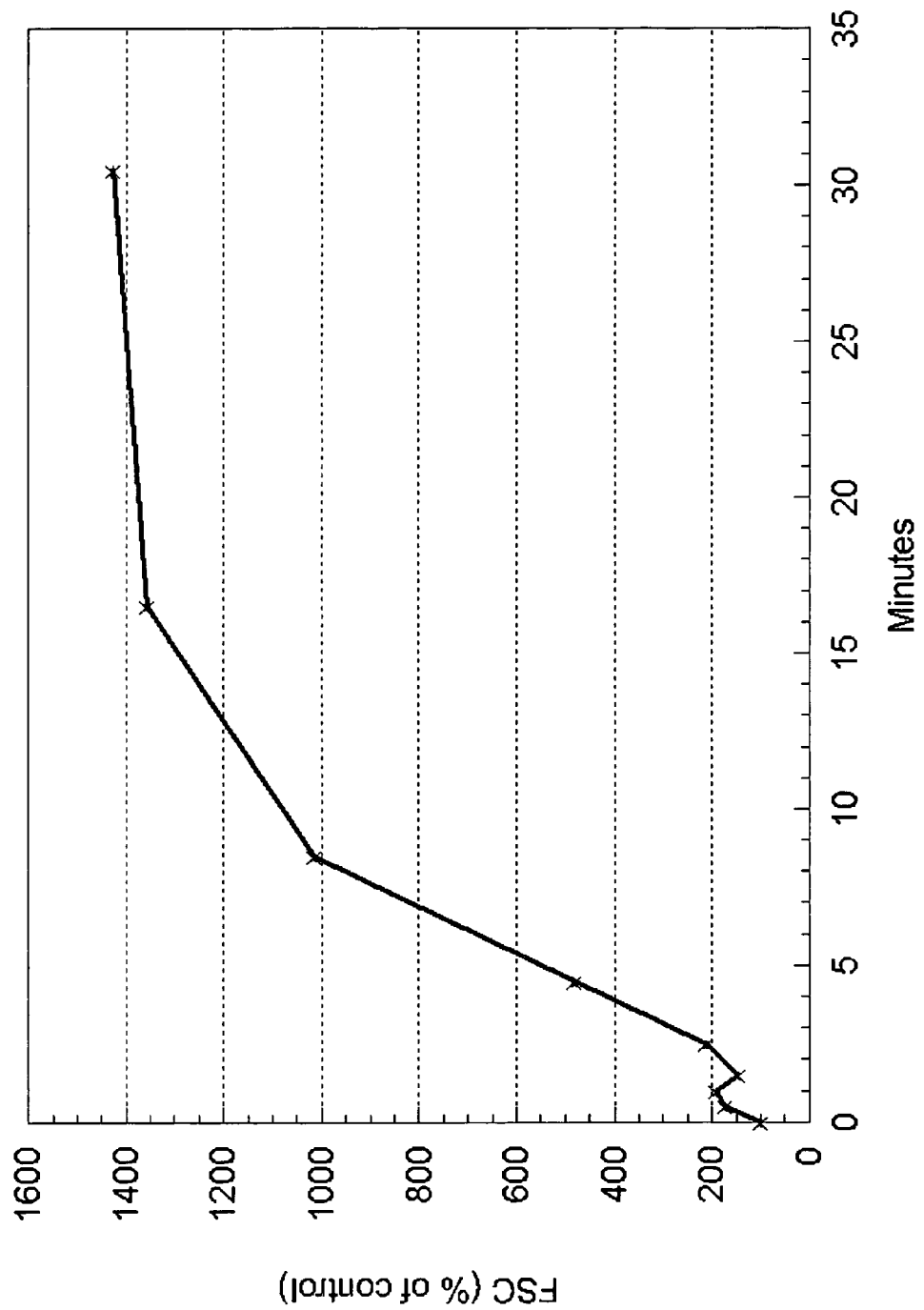
Figure 16: Time Course of FSC Changes in Response to MCP-1 Stimulation

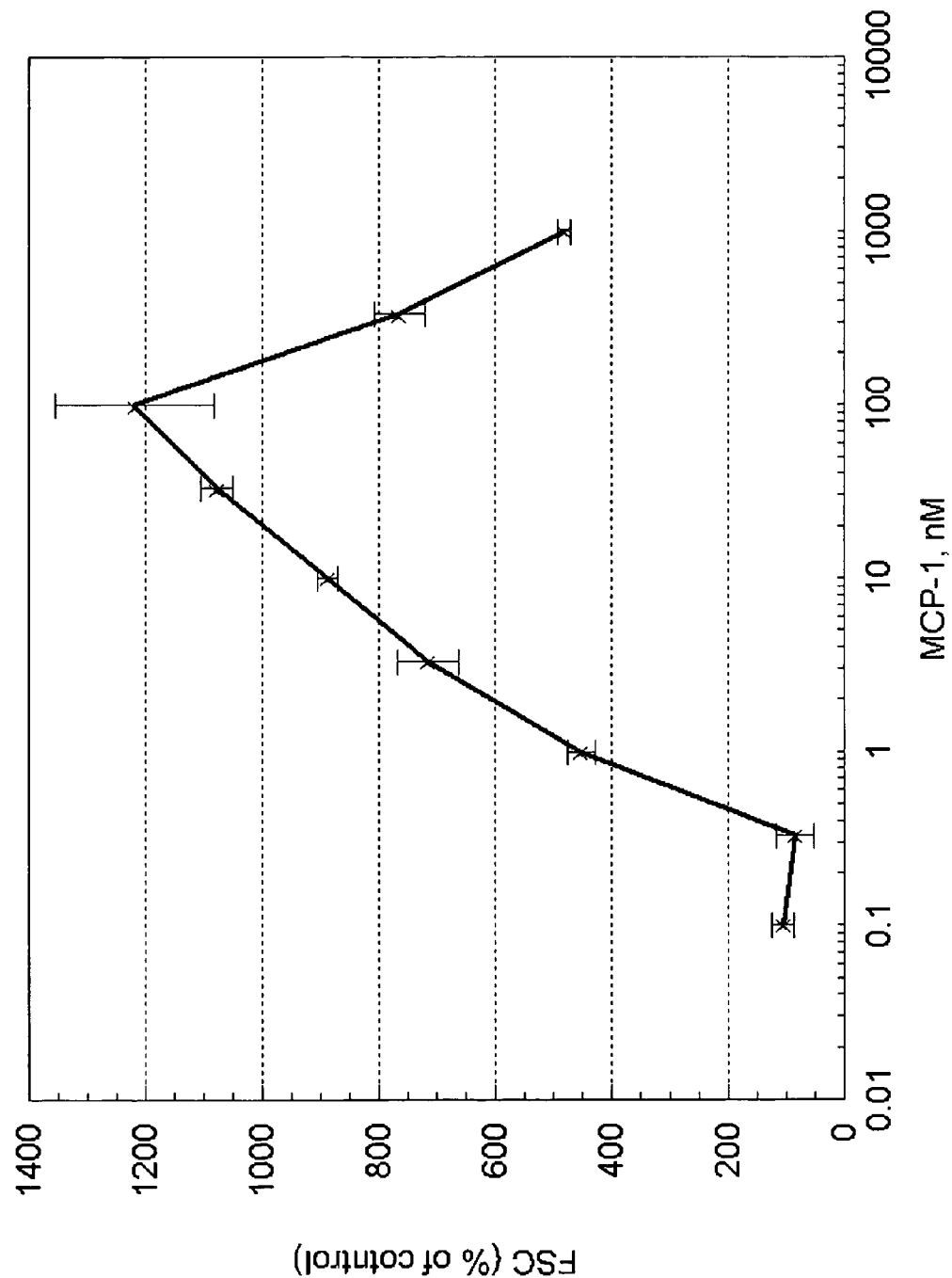

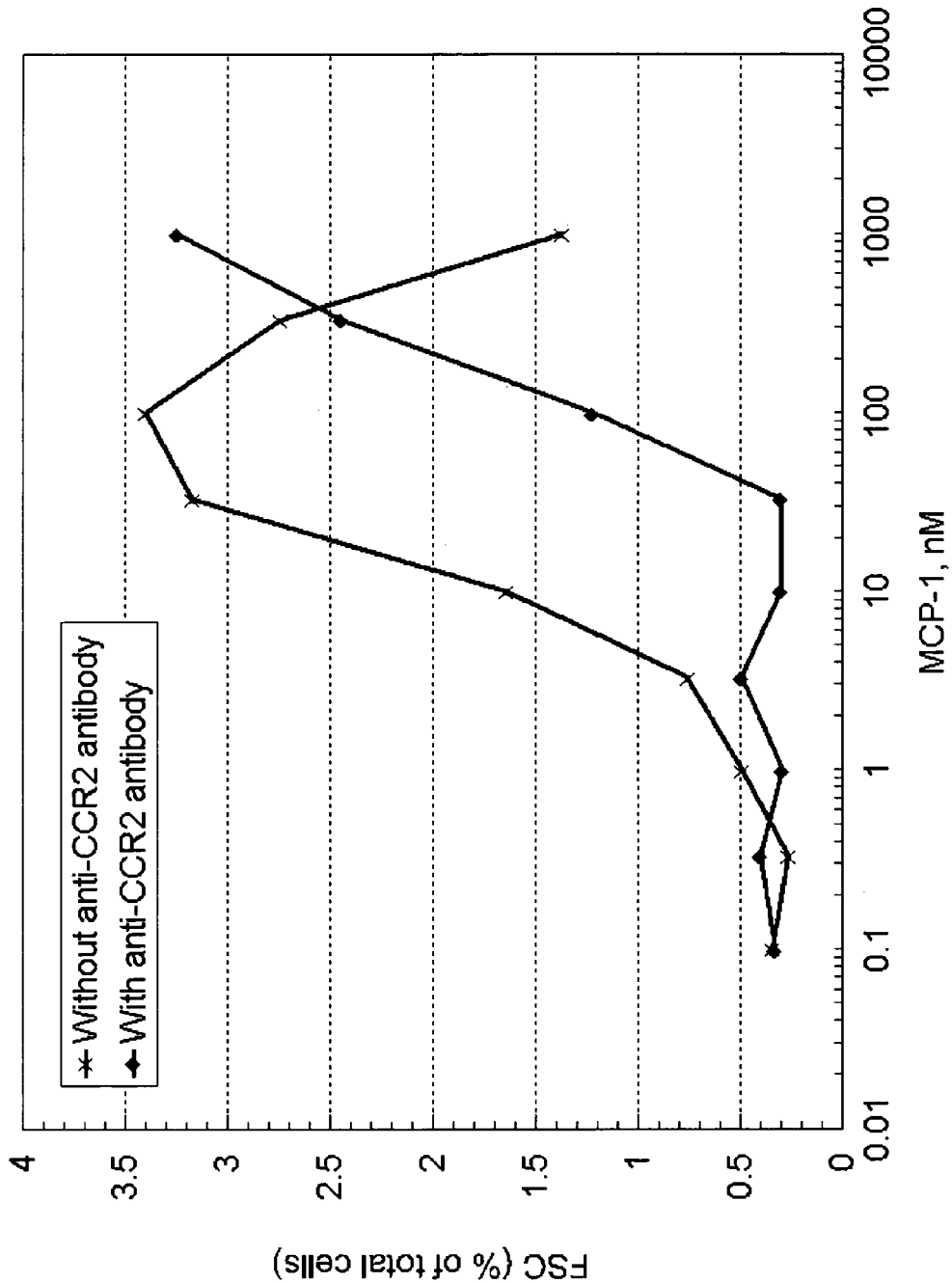

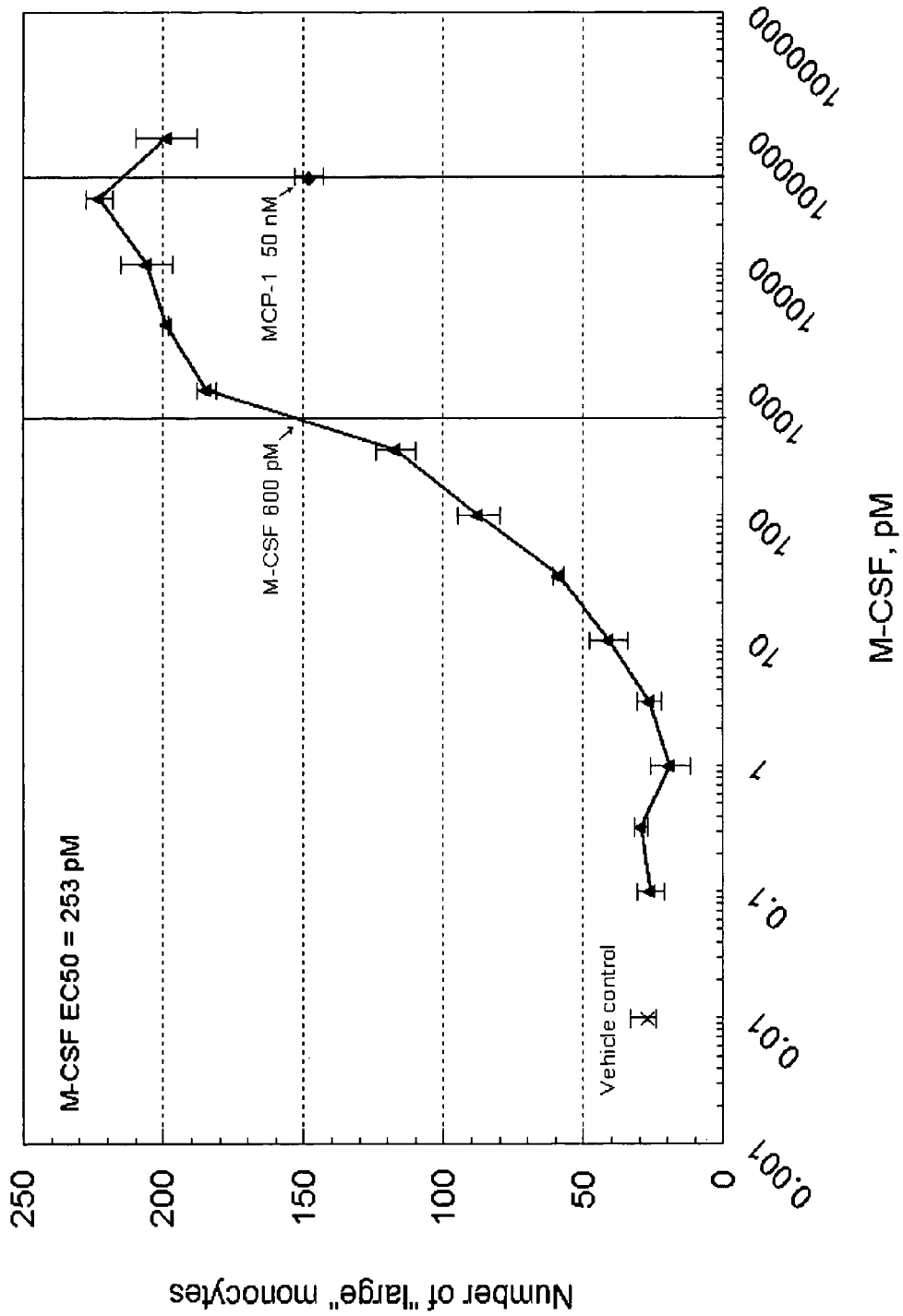
Figure 19: Effect of M-CSF on human monocyte shape change - comparison to MCP-1

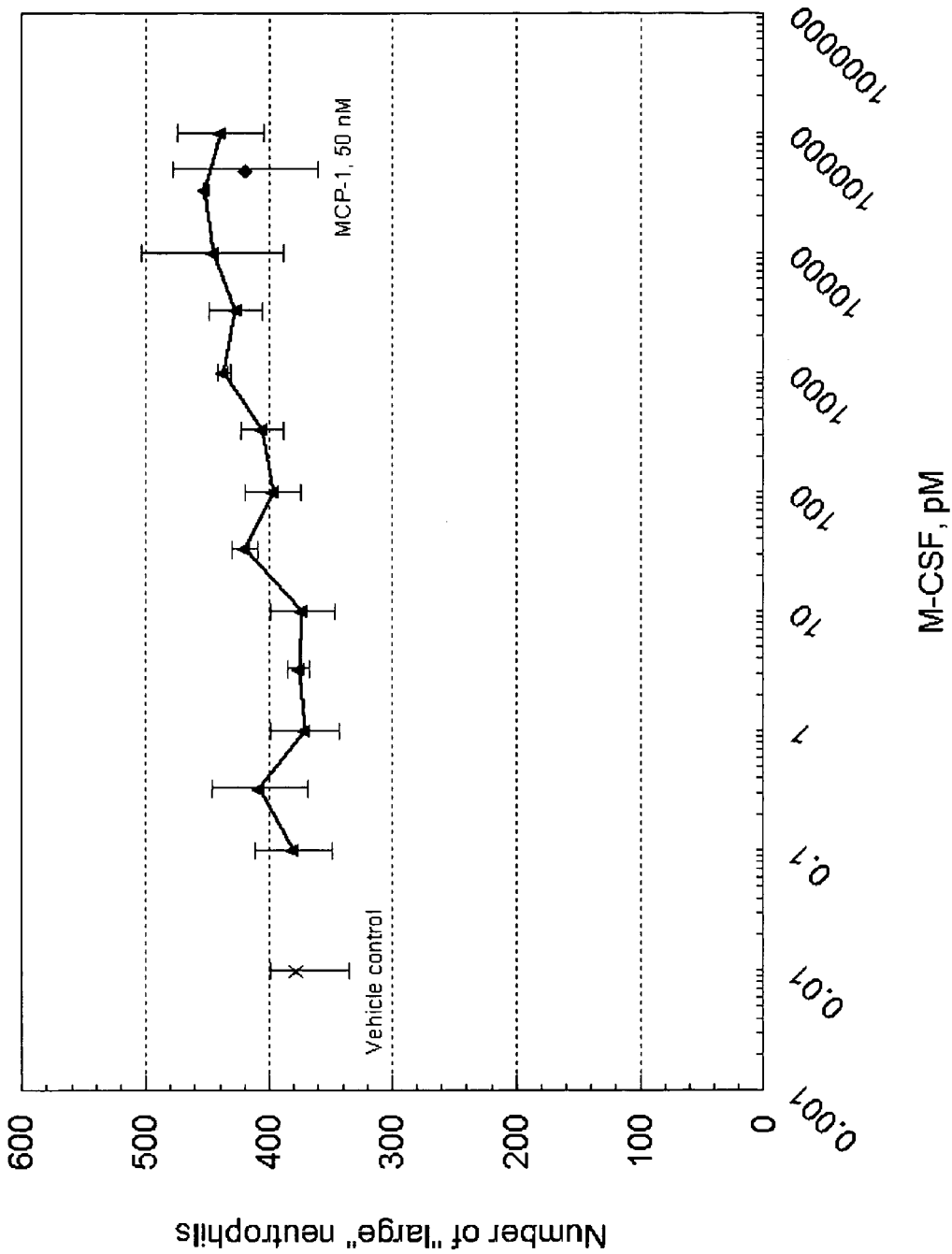

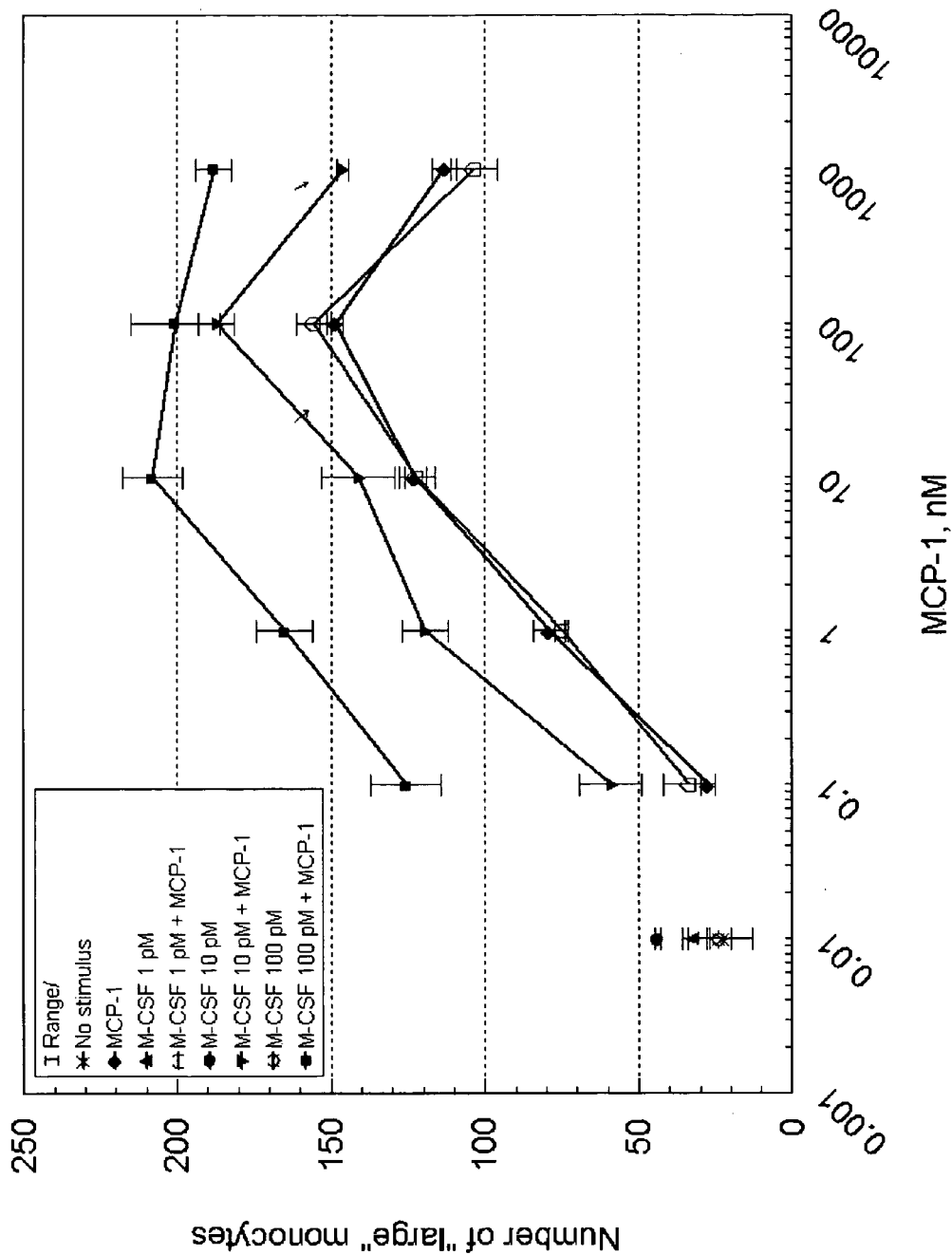

METHODS OF TREATING INFLAMMATION USING ANTIBODIES TO M-CSF

"This application claims priority of Ser. No. 60/190,842, filed Mar. 20, 2000."

FIELD OF THE INVENTION

The present invention is directed to inhibitors of haematopoetic factors called colony stimulating factors and methods of treating diseases responsive to inhibition of colony stimulating factors. The present invention is also directed to assays for screening inhibitors of CSF.

BACKGROUND OF THE INVENTION

Colony stimulating factors (CSFs) stimulate the differentiation and/or proliferation of bone marrow cells. CSFs in both human and murine systems have been identified and distinguished according to their activities involving two of the three main classes of leukocytes, namely granulocytes and monocytes. For example, granulocyte-CSF (G-CSF) and macrophage-CSF (M-CSF) stimulate the in vitro formation of neutrophilic granulocyte and macrophage colonies, respectively, while granulocyte-macrophage CSF (GM-CSF) has broader activities and stimulates the formation of both macrophage, neutrophilic, and eosinophilic granulocyte colonies. These CSFs act via their respective receptors, namely G-CSFR, M-CSFR, and GM-CSFR. G-CSR is expressed on multipotential hematopoietic progenitor cells and cells of myeloid lineage, and is important for regulation of granulopoiesis.

Evidence of the role G-CSF and G-CSFR play in inflammation includes the discovery that G-CSF is frequently found elevated in serum of and at inflammatory sites in patients with infections. The undetectable normal circulating levels of G-CSF ($\leq 10$ pM) increase in inflammatory conditions to a range of from 100 to 2000 pM. Further, transgenic mice with neutrophils expressing chimeric receptors with extra-cellular G-CSFR and intra-cellular erythropoietin receptor appear to retain their normal hematopoietic function but no longer respond to chemotactic signals. Also, the chemokine interleukin-8 (IL-8) fails to induce chemotaxis of neutrophils from G-CSFR −/− mice (i.e., G-CSFR knockout mice), suggesting a specific role for G-CSFR in neutrophil chemotaxis. However, by itself, G-CSF is a relatively weak chemoattractant.

Additionally, M-CSF, also known as colony stimulating factor-1, has been shown to increase blood and tissue macrophage numbers in several species. For example, it is known that M-CSF is produced within the joint in human rheumatoid arthritis, where it has been shown to cause severe exacerbation of the disease. This is consistent with other studies, wherein M-CSF was found to worsen the disease course of experimental disseminated candidiasis, a disease with many of the characteristics of tumor necrosis factor-mediated pathology. M-CSF was also found to stimulate secretion of urokinase plasminogen activator, which plays a role in proteolytic joint destruction. Recently, cDNA encoding the primary growth and differentiation factor for M-CSF has been isolated, sequenced and expressed, and human recombinant M-CSF is now available for experimental studies.

However, CSFs are not the only cytokines involved in inflammation. Also involved are chemokines, which are chemotactic cytokines that are released by a wide variety of cells to attract macrophages, T cells, eosinophils, basophils, and neutrophils to sites of inflammation. There are two classes of chemokines, the members of each class share an organizing primary sequence motif. Alpha chemokines such as IL-8, neutrophil-activating protein-2 (NAP-2), and melanoma growth stimulatory activity protein (MGSA) are chemotactic primarily for neutrophils, whereas beta chemokines such as RANTES (regulation-upon-activation, normal T expressed and secreted), MIP-1 alpha (macrophage inflammatory protein), MIP-1 beta, MCP-1 (monocyte chemotactic protein-1), MCP-2, and MCP-3 are chemotactic for monocytes, T-cells, eosinophils, and basophils.

Chemokines bind specific cell-surface receptors belonging to the family of G-protein-coupled seven-transmembrane-domain proteins which are termed "chemokine receptors." Chemokines and chemokine receptors such as, for example, CCR-1, CCR-2, CCR-2a, CCF-2b, CCR-3, CCR-4, CCR-5, CXCR-1, CXCR-2, CXCR-3, and CXCR-4, play a role in inflammation and autoimmune responses by attracting leukocytes, which migrate out of the microvasculature and into the extravascular space in response to chemoattractant molecules. These chemoattractants, which include cytokines and activated complement components, may be released by the patient or they may be released from an invading organism. Once exposed to chemoattractants within the vasculature, the leukocytes become activated and capable of adhering to the endothelium, providing the first step in the development of inflammation. Stimulated neutrophils adhere to the endothelium of the microvasculature in response to a gradient of chemoattractants which direct the cells into the extravascular space toward the source of the chemoattractant.

One chemokine in particular that mediates inflammatory response is IL-8. IL-8 is a cytokine that promotes the recruitment and activation of neutrophil leukocytes and represents one of several endogenous mediators of the acute inflammatory response. In the past it was variously termed neutrophil-activating factor, monocyte-derived neutrophil chemotactic factor, IL-8, and neutrophil-activating peptide-1. The term "IL-8" has gained the widest acceptance and will be used herein.

Evidence of the involvement of IL-8 in inflammatory responses includes the observation that neutralizing antibodies to human IL-8 were shown to have a protective effect in inflammatory lung injury in rats.

Further, preliminary nonhuman primate studies have confirmed the activity of IL-8 on hematological parameters. IL-8 was administered by both bolus and continuous infusion to baboons. This resulted in a rapid, transient and severe granulocytopenia followed by granulocytosis that persisted as IL-8 levels remained detectable within the circulation. Histopathological examination revealed a mild to moderate neutrophil margination in the lung, liver and spleen which was of greater severity in animals receiving the continuous infusion of IL-8.

Also, high levels of intravascular IL-8 have been reported in systemic conditions such as septic shock.

Further, it is known that IL-8 binds with a higher affinity to CXCR-1 than to CXCR-2. On the other hand, a primary receptor for MCP-1 is CCR-2, which is expressed predominately on macrophages.

Another chemokine that mediates inflammatopry response is MCP-1. Studies using animal macrophages have demonstrated the pivotal roles of MCP-1 in rheumatoid arthritis and atherosclerosis. Unfortunately, work on human macrophages has been hampered by the relative small number of these cells in human blood.

Historically, persons skilled in the pharmaceutical and medical arts have sought to increase levels of CSFs in patients, believing that CSFs provided therapeutic benefits to patients suffering from certain diseases and disorders. We have now unexpectedly discovered that CSFs synergistically enhance the chemoattractant effects of chemokines on recruitment of leukocytes to sites of inflammation. For example, it is shown below that G-CSF synergistically enhances the chemoattractant effects of IL-8 on the recruitment of neutrophils, and M-CSF synergistically enhances the chemoattractant effects of MCP-1 on the recruitment of monocytes. As IL-8 and MCP-1 are key mediators of inflammatory diseases, it would be desirable to identify substances capable of inhibiting the synergistic interactions of CSFs and chemokines for use in the treatment of diseases responsive to this inhibition.

We have now unexpectedly discovered useful methods for determining the ability of a compound, or a pharmaceutically acceptable salt thereof, to inhibit a synergistic interaction between a CSF and a chemokine, including a method for rapidly screening large numbers of such compounds. Accordingly, one embodiment of the present invention is a method for screening compounds, or pharmaceutically acceptable salts thereof, for inhibition of a synergistic interaction between a CSF and a chemokine. All that is needed to practice this embodiment of the present invention is to assay a potential inhibitor of said synergistic interaction according to the methods described below.

Another embodiment of the present invention is an inhibitor of a synergistic interaction between a CSF and a chemokine, which inhibitor is identified using a screening method of the present invention.

Further, another embodiment of the present invention is an inhibitor of a synergistic interaction between a CSF and a chemokine.

Still further, another embodiment of the present invention is a method of treating diseases and disorders responsive to inhibition of a synergistic interaction between a CSF and a chemokine.

Still further, another embodiment of the present invention is a pharmaceutical composition comprising an inhibitor of a synergistic interaction between a CSF and a chemokine, or a pharmaceutically acceptable salt thereof, and a pharmaceutically acceptable carrier, diluent, or excipient.

All that is needed to practice the present invention is to administer from one to six times daily a therapeutically effective amount of an inhibitor, or a pharmaceutically acceptable salt thereof, of a synergistic interaction between a CSF and a chemokine to a patient in need thereof for the treatment of inflammatory disorders and diseases responsive to inhibition of a synergistic interaction between a CSF and a chemokine. Determination of proper dosage, pharmaceutically composition, and form of administration of the inhibitor is well within ordinary skill in the pharmaceutical and medical arts.

U.S. Pat. No. 4,504,586 discloses murine-derived hybridoma tumor cell lines and monoclonal anti-Colony Stimulating Factor Subclass Number 1 antibody substances produced by these cell lines. Use of said monoclonal antibody substances, alone or in combination, in immunological procedures for isolation of natural Colony Stimulating Factor Subclass Number 1 and for quantitative detection of colony Stimulating Factor Subclass Number 1 in fluid samples.

SUMMARY OF THE INVENTION

The present invention is connected to the discovery that CSFs appear to be critical for leukocyte recruitment, specifically polymorpho-nuclear neutrophil (PMN) and monocyte recruitment, and exhibit synergizing activity with chemokines. Inhibition of the synergistic interactions between CSFs and chemokines useful in the present invention includes inhibition of the interaction between a CSF and a chemokine, and between a CSF and its receptor. Accordingly, inhibitors especially useful in the present invention include compounds capable of binding to a CSF, and thereby inhibiting the interaction between the CSF and a chemokine or the CSF receptor. Also especially useful inhibitors in the present invention include compounds capable of binding to a CSF receptor, and thereby inhibiting the interaction between the receptor at its CSF. Thus, inhibitors of the present invention include compounds which are antibodies directed against a CSF or a CSF receptor, small molecules capable of binding a CSF, and antagonists of CSF receptor.

One embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a colony stimulating factor receptor (CSFR), an antibody directed to a CSF or a CSFR, or an agent which inhibits activation of a CSFR, or a pharmaceutically acceptable salt thereof.

A preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is a monocyte-colony stimulating factor (M-CSF).

Another preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the chemokine is a beta-chemokine.

A more preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is an M-CSF, the chemokine is monocyte chemotactic protein-1 (MCP-1), and the inhibitor is an antibody directed to an M-CSF or an antibody directed to a monocyte-colony stimulating factor receptor (M-CSFR).

Especially preferred are said inhibitors which are monoclonal antibodies to an M-CSFR or M-CSF.

Another more preferred embodiment of the present invention is an inhibitor of a CSF which inhibits the synergistic effect of said° CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is an M-CSF, the chemokine is MCP-1, and the inhibitor is an antagonist of an M-CSFR.

Another preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is a granulocyte-colony stimulating factor (G-CSF).

Another preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the chemokine is an alpha-chemokine.

A more preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is a G-CSF, the chemokine is IL-8, and the inhibitor is an antibody directed to a G-CSF or an antibody directed to a granulocyte-colony stimulating factor receptor (G-CSFR).

Especially preferred are said inhibitors which are monoclonal antibodies to a G-CSF or G-CSFR.

Another more preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is a G-CSF, the chemokine is IL-8, and the inhibitor is an antagonist of a G-CSFR.

Another preferred embodiment of the present invention is an inhibitor of a CSF which inhibits the synergistic effect of said CSF on chemokine-mediated inflammation, osteoporosis, an autoimmune disease, or atherosclerosis, comprising an agent which binds to a CSF, an agent which inhibits expression of a CSF, an antagonist of a CSFR, an antibody directed to a CSF or a CSFR, or an agent which inhibits activation of a CSFR, or a pharmaceutically acceptable salt thereof, wherein the CSF is a GM-CSF.

Another embodiment of the present invention is a pharmaceutical composition, comprising an inhibitor of a CSF which inhibits the synergistic effect of said CSF on chemokine-mediated inflammation, osteoporosis, an autoimmune disease, or atherosclerosis, or a pharmaceutically acceptable salt thereof, and a pharmaceutically acceptable carrier, diluent, or excipient.

Another embodiment of the present invention is a method of treating inflammation, osteoporosis, an autoimmune disease, or atherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or atherosclerosis, or a pharmaceutically acceptable salt thereof.

Preferred is a method of treating inflammation, osteoporosis, an autoimmune disease, or atherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or atherosclerosis, or a pharmaceutically acceptable salt thereof, wherein the disease being treated is atherosclerosis.

Also preferred is a method of treating inflammation, osteoporosis, an autoimmune disease, or atherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or atherosclerosis, or a pharmaceutically acceptable salt thereof, wherein the disease being treated is sepsis.

Also preferred is a method of treating inflammation, osteoporosis, an autoimmune disease, or atherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or atherosclerosis, or a pharmaceutically acceptable salt thereof, wherein the disease being treated is asthma.

Also preferred is a method of treating inflammation, osteoporosis, an autoimmune disease, or atherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or atherosclerosis, or a pharmaceutically acceptable salt thereof, wherein the disease being treated is an autoimmune disease.

Also preferred is a method of treating inflammation, osteoporosis, an autoimmune disease, or artherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or artherosclerosis, or a pharmaceutically acceptable salt thereof, wherein the disease being treated is osteoporosis.

Also preferred is a method of treating inflammation, osteoporosis, an autoimmune disease, or artherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or artherosclerosis, or a pharmaceutically acceptable salt thereof, wherein the disease being treated is rheumatoid artritis.

Also preferred is a method of treating inflammation, osteoporosis, an autoimmune disease, or artherosclerosis, comprising administering to a mammal in need thereof a therapeutically effective amount of an inhibitor of a CSF which inhibits the synergistic effect of said CSF on chemokine-mediated inflammation, osteoporosis, an autoimmune disease, or artherosclerosis, or a pharmaceutically acceptable salt thereof, wherein the disease being treated is osteoarthritis.

The preferred use of the inhibitors of the present invention is for, but not limited to, the treatment of atherosclerosis, osteoporosis, and chronic and acute inflammatory and autoimmune diseases such as SLE, GVHD, RA, IBD, asthma, and psoriasis.

Another embodiment of the present invention is a method for screening for an inhibitor of an M-CSF which inhibits the synergistic effect of said CSF on chemokine-mediated inflammation, osteoporosis, an autoimmune disease, or atherosclerosis, comprising analyzing an (M-CSF)-stimulated monocyte population using a Fluorescent Activated Cell Sorter (FACS).

Preferred is a method for screening for an inhibitor of an M-CSF which inhibits the synergistic effect of said CSF on chemokine-mediated inflammation, osteoporosis, an autoimmune disease, or atherosclerosis, comprising analyzing an (M-CSF)-stimulated monocyte population using a FACS, wherein the (M-CSF)-stimulated monocyte population is analyzed in whole blood after red blood cell lysis.

Also preferred is a method for screening for an inhibitor of an M-CSF which inhibits the synergistic effect of said CSF on chemokine-mediated inflammation, osteoporosis, an autoimmune disease, or atherosclerosis, comprising analyzing an (M-CSF)-stimulated monocyte population using a FACS, wherein the screening method is a high throughput screening method.

Also preferred is a method for screening for an inhibitor of an M-CSF which inhibits the synergistic effect of said CSF on chemokine-mediated inflammation, osteoporosis, an autoimmune disease, or atherosclerosis, comprising analyzing an (M-CSF)-stimulated monocyte population using a FACS, wherein the (M-CSF)-stimulated monocyte population has also been stimulated by MCP-1.

Also preferred is a method for screening for an inhibitor of an M-CSF which inhibits the synergistic effect of said CSF on chemokine-mediated inflammation, osteoporosis, an autoimmune disease, or atherosclerosis, comprising analyzing an (M-CSF)-stimulated monocyte population using a FACS, wherein the (M-CSF)-stimulated monocyte population which has also been stimulated by MCP-1, is analyzed in whole blood after red blood cell lysis.

Another embodiment of the present invention is a method for screening for an inhibitor of a G-CSF which inhibits the synergistic effect of said CSF on chemokine-mediated inflammation, osteoporosis, an autoimmune disease, or atherosclerosis, comprising measuring binding of an ($I^{125}$) G-CSF to a G-CSFR in a (G-CSF)-stimulated neutrophil population.

Preferred is a method for screening for an inhibitor of a G-CSF which inhibits the synergistic effect of said CSF on chemokine-mediated inflammation, osteoporosis, an autoimmune disease, or atherosclerosis, comprising measuring binding of an ($I^{125}$) G-CSF to a G-CSFR in a (G-CSF)-stimulated neutrophil population, wherein the screening method is a high throughput screening method.

Another embodiment of the present invention is a method for screening for an inhibitor of a GM-CSF which inhibits the synergistic effect of said CSF on chemokine-mediated inflammation, osteoporosis, an autoimmune disease, or atherosclerosis, comprising measuring binding of an ($I^{125}$) GM-CSF to a GM-CSFR in a (GM-CSF)-stimulated neutrophil population or analyzing a (GM-CSF)-stimulated monocyte population using a FACS.

Another embodiment of the present invention is a method for screening for an inhibitor of a CSF which inhibits the synergistic effect of said CSF on chemokine-mediated inflammation, osteoporosis, an autoimmune disease, or atherosclerosis, the method comprising:

Step (a) Obtaining CSFR cDNA and corresponding ($I^{125}$)-CSF;

Step (b) Cloning the CSFR cDNA of Step (a) into a vector;

Step (c) Stably transfecting the vector of Step (b) into a hematopoetic cell line that resembles circulating leukocytes;

Step (d) Quantitating the transfected vector of Step (c) and measuring the binding of said ($I^{125}$)-CSF; and Step (e) Screening agents for inhibition of CSF activity using a binding assay comprising the transfected vector of Step (c) and said ($I^{125}$)-CSF.

Another embodiment of the present invention is an inhibitor of a CSF that inhibits the synergistic effect of said CSF on chemokine-mediated inflammation, osteoporosis, an autoimmune disease, or atherosclerosis, which inhibitor is identified using one of the methods for screening for said inhibitors described above.

Because leukocytes are important mediators of inflammatory and immunoregulatory disorders and diseases, agents which inhibit or prevent leukocyte accumulation or activation by inhibiting the synergistic effect of a CSF on chemokine induced leukocyte-mediated inflammation, osteoporosis, an autoimmune disease, or atherosclerosis will be useful in such disorders and diseases. The present invention, therefore, also provides an antagonist of CSF capable of inhibiting or minimizing the attractive capabilities of chemokines for leukocytes and of inhibiting or minimizing leukocyte accumulation and/or activation in vitro and in vivo.

The present invention further provides screens or assays for identifying agents that inhibits or otherwise hinders the binding of a CSF to a CSF receptor, for example, any agent that binds to a CSF or to a CSF receptor. Screens that can be employed in the identification of such antagonists/agonists are known to those of skill in the art. The different methods one could use to identify antagonists or agonists of CSF receptors include, but are not limited to: (1) Look for G-CSF binding to its receptor on the cells over expressing the G-CSF receptor; (2) Look for down stream kinase activations and develop a high throughput assay; (3) Look for the transcription factor activations (such as STATs) as a functional read out in reporter gene assays amenable for high throughput screening.

The present invention also provides an agent that inhibits or otherwise hinders the production, release or action of a CSF, especially an agent as described above, for use as a medicament. The invention also provides the use of an agent that inhibits or otherwise hinders the production, release or action of a CSF, especially an agent as described above, in the manufacture of a medicament for the treatment of asthma or another disease having an inflammatory component, particularly with accumulation of neutrophils, for example in ischemia reperfusion or acute respiratory distress or eosinophils, for example, rhinitis or eczema, especially allergic eczema syndrome.

BRIEF DESCRIPTION OF THE DRAWINGS

FIGS. 1 to 21 of the accompanying drawings illustrate the present invention. The following is a brief description of the Figures. A more detailed description of the Figures is given below and in the Examples section of this specification.

FIG. 1 illustrates that G-CSF synergizes IL-8 induced PMN chemotaxis.

FIG. 2 illustrates that GM-CSF synergizes IL-8 induced PMN chemokines.

FIG. 3 illustrates the dose response curve for IL-8 with fixed concentration of G-CSF.

FIG. 4 illustrates that G-CSF does not synergize f-MLP induced neutrophil chemotaxis.

FIG. 5 illustrates that G-CSF enhances IL-8 induced in vivo neutrophil intradermal recruitment.

FIG. 6 illustrates the binding of $I^{125}$ G-CSF on polymorphonucleocytes (PMN).

FIG. 7 illustrates that G-CSF neutralizing antibody inhibits G-CSF synergized chemotaxis.

FIG. 8 illustrates that G-CSF pre-incubation alters PMN chemotactic response to IL-8.

FIG. 9 illustrates that G-CSF does not alter IL-8 induced calcium flux.

FIG. 10 illustrates that G-CSF does not increase IL-8 binding on PMNs.

FIG. 11 illustrates that G-CSF pre-incubation does not alter IL-8 binding.

FIG. 12 illustrates that G-CSF pre-incubation alters PMN response to IL-8.

FIG. 13 illustrates that G-CSF potentiates both chemotactic and chemokinetic responses to IL-8.

FIG. 14 illustrates that the three separate subpopulations of leukocytes can be detected by FACS.

FIG. 15 illustrates that stimulation of human whole blood by MCP-1 causes an increase in the number of monocytes.

FIG. 16 illustrates the time course of forward scatter detection of monocytes in response to stimulation of human whole blood by MCP-1.

FIG. 17 illustrates a dose response curve plotting forward scatter detection of monocytes in human whole blood versus concentration of MCP-1.

FIG. 18 illustrates the inhibitory effects of an anti-CCR-2 antibody on MCP-1 stimulation of human whole blood.

FIG. 19 illustrates the effect of M-CSF on human monocyte size.

FIG. 20 illustrates the lack of effect of M-CSF on human neutrophil size.

FIG. 21 illustrates the synergistic effect of M-CSF and MCP-1 on human monocyte size.

DETAILED DESCRIPTION OF THE INVENTION

The present invention is directed to inhibitors of haematopoetic factors called colony stimulating factors and methods of treating diseases responsive to inhibition of colony stimulating factors (CSFs). The present invention is also directed to assays for screening inhibitors of CSF.

The present invention relates to the ability of CSFs to synergize the attractive capabilities of chemokines to leukocytes, preferably PMNs or monocytes. As discussed in the examples below, G-CSF appears to be critical for neutrophil recruitment and exhibits synergizing activity with IL-8, and M-CSF appears to be critical for macrophage recruitment and exhibits synergizing activity with MCP-1.

The inhibitors of the present invention have an important role in asthma and in other diseases having an inflammatory component where leukocyte accumulation and/or activation is a prominent feature, for example, an autoimmune disease, rheumatoid arthritis, osteoarthritis, atherosclerosis, rhinitis, and eczema, especially allergic eczema. Accordingly, agents that inhibit or otherwise hinder the production, release or action of CSFs have potential as selective therapeutic agents. Such agents and their therapeutic use are part of the present invention.

Preferred inhibitors of the present invention are inhibitors of M-CSF, including antibodies directed to M-CSF, especially monoclonal antibodies, and antagonists of M-CSFR. Preferred methods of treating of the present invention are methods employing the inhibitors of M-CSF of the present invention.

In order to provide an understanding of several of the terms used in the specification and claims, the following definitions are provided:

CSFs are defined to include the classic structurally distinguishable chemokines based on the C-terminal cysteine arrangement, as opposed to the peptide f-Met-Leu-Phe (f-MLP), which does not belong to the classic chemokine classes.

The term "comprising", which is synonymous with the terms "including", "containing", or "characterized by" is inclusive or open-ended and does not exclude additional, unrecited elements or method steps from the scope of the invention that follows.

The phrase "consisting of" is closed-ended and excludes any element, step, or ingredient not specified in the description of the invention that follows.

The phrase "consisting essentially of" limits the scope of the invention that follows to the specified elements or steps and those further elements or steps that do not materially affect the basic and novel characteristics of the invention.

$EC_{50}$: The effective concentration of an agent required to produce 50% of a maximal response.

Biological Activity: The term biological activity is a function or set of functions performed by a molecule in a biological context (i.e., in an organism or an in vitro surrogate or facsimile model). For IL-8 or other alpha chemokine biological activity is characterized by its chemotactic activity (preferably PMNs, but may also include T lymphocytes and/or monocytes/macrophages).

Leukocyte: A white blood cell which may be a granulocyte, lymphocyte, or monocyte.

Chemokine: A biological molecule capable of attracting a subset of cell population from the circulating blood to the site of its presence in a gradient dependent fashion. There are two classes of chemokines, the members of each class share an organizing primary sequence motif. The alpha chemokines, such as IL-8, neutrophil-activating protein-2 (NAP-2), and melanoma growth stimulatory activity protein (MGSA) are chemotactic primarily for neutrophils, whereas beta chemokines, such as RANTES (regulation-upon-activation, normal T expressed and secreted), MIP-1 alpha (macrophage inflammatory protein), MIP-1 beta, MCP-1 (monocyte chemotactic protein-1), MCP-2, and MCP-3 are chemotactic for monocytes, T-cells, eosinophils, and basophils.

PMN: Polymorpho-nuclear neutrophils represent the mature form of circulating leukocyte population that has evolved from the granulocytic lineage and that goes through the developmental stages of myeloblast, promyelocyte, myelocyte and metamyelocyte. PMNs primarily refer to neutrophils. Other cell types include the monocyte, which also comes from the same granulocyte lineage and evolves from promonocyte to monocyte.

Assay or Screen: A method used to evaluate the efficacy (agonism or antagonism) of the chemical compounds or biological factors in a given assay system. The system may be amenable for high throughput efficiency.

Modulate: An increase or decrease seen in a set pattern of activity in a system upon addition or deletion of another factor in the same system.

The phrase "autoimmune disease" means the diseases classified as "Highly probably" or "Probable" in TABLE 20-3. PUTATIVE AUTOIMMUNE DISORDERS of The Merck Manual of Diagnosis and Therapy, 16$^{th}$ edition, Robert Berkow, ed., Merck Research Laboratories, Rahway, N.J., 1992, page 340, which is hereby incorporated herein by reference. Diseases classified as highly probable include, to name a few, systemic lupus erythematosus, Grave's disease, myasthenia gravis, insulin resistance, and autoimmune hemolytic anemia. Diseases classified as probable include, to name a few, rheumatoid arthritis, scleroderma with anti-collagen antibodies (Abs), pernicious anemia, and some cases of diabetes mellitus.

The term "atherosclerosis" means diseases in which the walls of medium- and large-diametered arteries become thickened and lose elasticity (see the Merck Manual of Diagnosis and Therapy, supra., 1992; 409–413).

Inflammatory diseases and disorders are diseases and disorders with an inflammatory component. Preferred inflammatory diseases and disorders include atherosclerosis, rheumatoid arthritis, osteoarthritis, asthma, and autoimmune diseases.

Osteoporosis is a generalized, progressive diminution in bone tissue mass per unit volume, causing skeletal weakness. Bone resorption is increased in osteoporosis, while rate of bone formation appears to be normal, although it may be defective in nature. Risk factors for osteoporosis include rheumatoid arthritis and chronic obstructive pulmonary disease (COPD), both of which are conditions with an inflammatory component.

It is to be appreciated that as used herein the phrases "antibodies to", "antibodies directed against", and "antibodies capable of binding with" are used interchangeably.

Further, it is to be appreciated that the terms "antibody" and "antibodies," as used herein, mean a human antibody or antibodies, respectively, which is/are directed against a human CSF. Development of such antibodies may be carried out, for example, by employing a mouse-derived cell line wherein mouse antibody genes have been knocked out and human antibody genes inserted instead. Mouse and other nonhuman, nonprimate-derived antibodies to a human CSF are not part of the present invention as these antibodies, when administered to a human, will cross react, usually in about 20 to 25 days. This cross reaction means the human host develops an immunological reaction to the nonhuman, nonprimate derived antibodies, which prohibits use of said antibodies in the treatment of human disease.

Inhibitors that affect the interaction of a CSF with CSF receptors, for example, by binding to a CSF or to a CSF receptor, inhibit a chemokine's attractive abilities to leukocytes and are part of the present invention. An example of such an inhibitor is receptors themselves which, on administration, can bind a CSF and prevent its interaction with naturally-occurring receptors. Such inhibitory receptors may be soluble or insoluble. Receptors which are not involved in cell activation may be bound to, or induced on, cells. Such receptors may also be used to remove endogenous CSF.

Further examples of inhibitors that inhibit the interaction of CSF with CSF receptors are receptor antagonists and antibodies, both antibodies directed against (capable of binding with) a CSF and antibodies directed against a CSF receptor. Especially preferred antibodies are monoclonal antibodies. Any other inhibitor that inhibits or otherwise hinders the binding of a CSF to a CSF receptor, including, for example, any other inhibitor that binds to a CSF or to a CSF receptor, also has therapeutic potential. Further, inhibitors that have therapeutic potential are also those that prevent or inhibit activation of CSF receptors.

Further, inhibitors that inhibit or otherwise hinder the action of CSFs are those that change the structure of a CSF such that it is no longer able to bind to a CSF receptor. One example of such an inhibitor is an enzyme or other agent that degrades CSF specifically.

Receptor promiscuity is common among CSFs, so although it is essential that a receptor is capable of binding a CSF, the receptor need not necessarily be M-CSF-specific or G-CSF-specific. For example, a receptor may bind GM-CSF, M-CSF, G-CSF, and/or other leukocyte attractant CSF.

As indicated above, possibilities for therapeutic intervention include the use of a receptor to which a CSF binds, especially a soluble receptor. It may be advantageous to use a CSF-specific receptor. Further possibilities for therapeutic intervention include receptor antagonists, for example, based on 3-dimensional structures or the amino acid sequences of CSFs and/or of CSF receptors, and agents found to inhibit CSF or other agonists binding to or activating CSF receptors.

Inhibitors that prevent or inhibit CSF synthesis or release may also be used therapeutically. Such agents and their use are also part of the present invention.

All inhibitors of CSF activity, synthesis, and release, including soluble receptors, antibodies, antagonists and inhibitors of agonist binding, and their use are part of the present invention.

It is also to be appreciated that the inhibitors of the present invention may have chiral centers, in which case all stereoisomers thereof, both separately and as racemic and/or diastereoisomeric mixtures, are included.

Some of the inhibitors of the present invention are capable of further forming nontoxic pharmaceutically acceptable acid addition and/or base salts. All of these forms are within the scope of the present invention.

For example, pharmaceutically acceptable acid addition salts of the inhibitors of the present invention include salts derived from inorganic acids such as hydrochloric, nitric, phosphoric, sulfuric, hydrobromic, hydriodic, hydrofluoric, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihyrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66: 1–19.

The acid addition salts of basic inhibitors of the present invention are prepared by contacting the free base form of the inhibitors with a sufficient amount of the desired acid to produce the salt in the conventional manner. Usually, 1 mol equivalent of desired acid is contacted with 1 mol equivalent of the inhibitor.

Pharmaceutically acceptable base salts of inhibitors of the present invention are formed with metal cations such as alkali and alkaline earth metal cations or organic ammonium compounds. Examples of metal cations used are cations of sodium, potassium, magnesium, calcium, and the like. An organic ammonium compound is formed by protonation of the corresponding organic amine. Examples of suitable organic amines are N,N-dibenzylethylenediamine, chloroprocaine, choline, diethanolamine, dicyclohexylamine, ethylenediamine, N-methylglucamine, and procaine (see, for example, Berge, supra., 1977).

Base salts of acidic inhibitors of the present invention are prepared by contacting the free acid form of the inhibitor with a sufficient amount of a suitable base that provides the desired metal cation or organic ammonium compound to produce a salt in the conventional manner. A suitable base that provides a desired metal cation includes alkali and alkaline metal cation hydroxides and carbonates. A suitable base that provides a desired organic ammonium compound is the free base of the corresponding organic amine. Usually, 1 mol equivalent of a suitable base that provides the desired metal cation or organic ammonium compound is contacted with 1 mol equivalent of the inhibitor.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Inhibitors of the present invention may be identified using in vivo and in vitro assays based on inhibition of chemoattraction and/or accumulation and/or activation of leukocytes by CSFs. Some general methods for testing the activity of a compound for an inhibitory effect on the activity of a chemoattractant chemokine in vitro are known. Such assays may be used to determine the inhibitory action of a putative inhibitor on in vitro effects induced in leukocytes by the synergistic activity of CSFs on chemokines.

Examples of in vitro and in vivo assays both for the determination of CSF activity and for the determination of CSF inhibitory activity are described herein. For example, Example 1 gives a detailed protocol for an in vitro assay of the present invention. The assays described herein may be used as such, or may be modified as required. Assays may be used alone or in combination with other assays known to those skilled in the art to establish CSF and CSF-inhibitory activity. A putative inhibitor of the present invention may be any of the types of molecules described above, including receptors, for example, soluble receptors, antibodies, and antagonists and inhibitors of agonist binding. A protocol screening assay for G-CSF receptor antagonists is described in Example 2.

A protocol screening assay for inhibitors of the synergistic effect of M-CSF on a chemokine-induced, monocyte-mediated inflammation, osteoporosis, an autoimmune disease, or atherosclerosis is described in Example 3.

Assays for inhibitors of a CSF include immunoassays, particularly enzyme-linked immunosorbent assays (ELISAs). The invention provides, for example, an immunoassay for an antigen, characterized in that the antigen is a CSF, and also provides an immunoassay for an antibody, characterized in that the antibody is an anti-CSF antibody. The invention also provides assays for CSFs that are analogous to immunoassays for CSFs, but that use a specific-binding partner other than an antibody. In such specific-binding partner assays, a CSF receptor, including a soluble CSF receptor, may be used instead of an anti-CSF antibody.

In an immunoassay, an anti-CSF antibody may, for example, be coated on a solid surface to enable capture and hence detection of CSF. An anti-CSF antibody may be used in an assay for the detection of antibodies to CSF, for example, in a competitive antibody assay. A labeled CSF or a derivative thereof, for example, a recombinant CSF or a synthetic peptide comprising part of the amino acid sequence of an CSF may be used in a competitive antigen assay for CSF or may be used to coat a solid surface in a capture assay for antibodies to CSF. The many different types of assay format are well described in the literature of the art, see for example "ELISA and Other Solid Phase Immunoassays, Theoretical and Practical Aspects" eds. Kemeny D. M. and Challacombe S. J., John Wiley, 1988: (36). Assays using an CSF receptor instead of an anti-CSF antibody may be carried out analogously.

The following examples are provided to further illustrate the present invention and are not intended to limit the invention beyond the limitations set forth in the appended claims.

EXAMPLE 1

Materials and Methods

Reagents & Animals: For all experiments, male New Zealand White rabbits (3.0–3.5 Kg) purchased from Charles River Breeding Lab (Wilmington, Mass.) were used. The animals were fed standard lab rabbit CHOW (Ralston Purina Company, St. Louis, Mo.) and housed according to institutional guidelines. G-CSF was obtained from R&D Laboratories (Minneapolis, Minn.); transwell plates for chemotaxis were obtained from Corning-Costar (Corning, N.Y.); LYMPHOPREP (Nyegaard & Co. A.S., Oslo, Norway) was obtained from Nycomed Pharma A.S., Oslo, Norway; prostaglandin $E_2$ ($PGE_2$) was obtained from Caymen Chemical (Ann Arbor, Mich.); bradykinin was obtained from Sigma Chemical Co. (St. Louis, Mo.); and $^{125}$I-IL-8 was obtained from Amersham Life Science, Budhinghamshire, England. IL-8 was a kind gift from Leukocyte, Inc. (Boston, Mass.).

Chemotaxis Assay: Peripheral circulating neutrophils were isolated from the blood of normal healthy volunteers. Heparinized venous blood was dextran sedimented followed by centrifugation over LYMPHOPREP and hypotonic lysis of contaminating red blood cells. Isolated neutrophil pellet was resuspended in supplemented RPMI media (sodium bicarbonate free RPMI with 50 mM of HEPES and 0.2% BSA). Chemotaxis assay was performed in the 3 μM transwell chambers. The cells were placed in the top chamber at a density of $1 \times 10^6$/well, and the chemoattractant (interleukin-8±G-CSF) was placed in the bottom chamber. In the G-CSF preincubation studies, cells were treated with G-CSF in the top chamber for the indicated time periods and then were subsequently exposed to IL-8 in the bottom chamber. In studies to assess chemokinesis, IL-8 and/or G-CSF was placed instead in the top chamber. Migration of neutrophils into the bottom chamber in response to the chemoattractant was monitored. The migrated neutrophils were quantitated by FACScan (Beckton Dickinson Immunocytometry Systems, San Jose, Calif.) analysis.

In Vivo Recruitment Assay: At t=0, rabbits received 14.5 ng/kg (10 μCi) $^{125}$I-IL-8 IV. At t=15 minutes rabbits were anesthetized with isoflurane and injected intradermally (100 μL/site) with 0.01–3.3 μg IL-8 or IL-8 and G-CSF (100 pM). The vehicle consisted of sterile saline supplemented with 0.2% bovine serum albumin and 0.01 mM $PGE_2$ and 0.1 μM bradykinin. At t=75 minutes, rabbits were euthanized with 1 mL IV dose of BEUTHANASIA (Burns Pharmaceuticals, Oakland, Calif.): -D Special (Shering-Plough Animal Health, Kenilworth, N.J.), and skin biopsies were obtained using a 6.35 mm diameter punch (O'Brien Consolidated Industries, Lewiston, Me.). The biopsies were weighed, and the radioactivity was determined using a gamma counter (Packard Model 05005, Downers Grove, Ill.).

Calcium Flux Assay: Calcium flux in response to IL-8 with or without G-CSF was assessed using standard fluorescent emission protocol. Briefly, neutrophils were loaded with 4 μm of Fluo-4, for one hour at 37° C. In a 96-well plate approximately 300,000 cells/well were preincubated with or without G-CSF (0.1 pM to 1000 pM) for the respective time periods indicated and then were subsequently stimulated with IL-8. Intracellular calcium flux in the cell was measured using FLIPR$^{384}$ (Molecular Devices, Sunnyvale, Calif.).

Binding Assay: The IL-8 and G-CSF binding assays were performed on the isolated human neutrophils using 0.3 mL micro sedimentation tubes (Sarstedt, Newton, N.C.). A small amount (9.5 μL) of sucrose solution (0.4%) was placed through the narrow tip of the tube by centrifugation. The reaction mix was layered gently on the sucrose solution to allow an air bubble in between the two solutions. In IL-8 binding studies, a total of 40,000 cells with 0.5 nM of hot IL-8 were used in each reaction. In cold competition studies, excess of 500 fold cold IL-8 was added. To quantitate the G-CSF binding on PMN, the cell number was varied from 50,000 to 1,000,000 per reaction with 5 nM of $^{125}$I G-CSF. In both binding studies, the cells were incubated with hot ligand for 3 hours and were pelleted at 10,000 RPM for 2 minutes. The sucrose layer was used to separate the bound from the unbound radio-labeled ligand. The cell pellet was cut out with a razor blade and the radioactive counts in the cell pellet were measured using a gamma counter.

In Vivo Experiment Data Analysis: In each experiment, triplicate samples were obtained for each experimental condition. Counts were adjusted by first subtracting out baseline control values, normalizing for differences in tissue weight, and adjusting the activity to that of a sample with a theoretical 100 mg tissue weight. In dose-response studies where the 1-μg dose of IL-8 was used, the weight-normalized background (vehicle-treated skin) was subtracted from weight-normalized treated samples, and the data was then expressed as a percent maximal response to the 1-μg dose of IL-8. The dose of 1 μg of IL-8 typically produces the approximate maximal recruitment response to IL-8. Normalizing the data with this method reduced the interanimal variability.

Statistical Analysis: All data are presented as mean ± standard deviation. Student t-test was used to compare between groups using JMP (SAS Institute Inc, Cary, N.C.) Version 3.0, statistical analysis software.

G-CSF was traditionally known to be a hematopoetic growth factor and also known to enhance functional capacities of the neutrophils through maturation of the cell. However, surprisingly, in G-CSF knockout mice, the circulating mature neutrophil number was less, but maturation was not defective, attributing additional roles for the traditionally known hematpoetic growth factor. Similar observations were made in G-CSF receptor knockout mice. In addition, it was observed that the neutrophils from G-CSF receptor knockout mice do not chemotax in response to IL-8 or f-MLP. Based on these studies, we proposed that a synergism exists between G-CSF and other chemokines for its functional activation, in vivo. Studies indicating that neutralizing G-CSF antibodies inhibit the G-CSF induced synergism supported the G-CSF-specific mechanism. Our studies, in vivo and in vitro support the synergistic mechanisms that exist between these molecules. In vivo, in inflammatory situations, picomolar concentrations of G-CSF are found at the site along with nanomolar concentrations of chemokines. Hence, it is quite possible that the synergistic mechanisms that we found here in the study are biologically significant. Hence, blocking the synergism using strategies that antagonize G-CSF or the receptor to prevent inflammation would be a useful tool to prevent the inflammatory process.

EXAMPLE 2

Protocol for a potential screening assay for G-CSF receptor antagonists:

This assay utilizes the binding properties of G-CSF directly to its receptor on the cells.

1. Obtain G-CSF receptor cDNA from the human genomic DNA synthesized from human neutrophils. The cDNA can be obtained by polymerase chain reaction (PCR) using primers aligned to the 5' and 3' ends of the mRNA sequence that is readily available in the IMPATH GENEBANK CANCER TISSUE/PERIPHERAL BLOOD REPOSITORY (IMPATH, Inc, Franklin, Mass.).

2. Clone the G-CSFR cDNA into a plasmid such as pcDNA 3.1 and stably transfect into a hematopoetic cell line that closely resembles the circulating leukocytes. Stably integrated clones can be screened by using an antibiotic resistance marker such as gentamycin (G418).

3. Using radiolabeled G-CSF, the expression of this transfected G-CSFR can be quantitated and the binding of G-CSF can be measured. The binding is performed using radiolabeled ($I^{125}$) G-CSF. ($I^{125}$)G-CSF is incubated with the stably transfected cells in a tube for 3 hours in the presence or absence of cold (i.e., not radiolabeled) G-CSF. After 3 hours, the unbound fraction of the radiolabeled G-CSF is separated using sucrose gradient separation technique. The cells with the bound radiolabeled G-CSF are pelleted, and the amount of incorporated radioactive material is measured using a scintillation counter. The amount of scintillation count is proportional to the amount of bound radiolabeled G-CSF, and a high ratio of radiolabeled G-CSF (to radiolabeled G-CSF plus non-radiolabeled G-CSF) binding indicates less nonspecific binding. Based on the binding, further experiments selecting for high expressing clones are performed.

4. To screen for G-CSFR antagonists, cells are first preincubated with the inhibitor of the present invention for 30 minutes, at which point, the radiolabeled G-CSF is added, and incubation is continued for 3 hours more. An antagonist will decrease the binding of the G-CSF to its receptor, and this decrease will be evident from the decreased binding of radiolabeled G-CSF on the cells.

5. The effective concentrations of the antagonists will be evaluated by performing a dose-response curve on the inhibitors of the present invention. An antagonist might represent a molecule that binds to the receptor and does not allow the receptor's ligand to bind, or it could be a compound that binds to the receptor's ligand and does not let the ligand bind to the receptor.

Similar protocols can be developed to screen for G-CSF antagonists using kinase assay systems or gene transcriptional activation systems using reporter constructs. All of these protocols are amenable for high throughput screening.

Protocols for screening inhibitors of the synergistic effect of M-CSF on a chemokine-induced monocyte-mediated inflammation, osteoporosis, an autoimmune disease, or atherosclerosis are described below, including Example 3.

EXAMPLE 3

The assay of Example 3 provides a method for directly measuring activation of human monocytes in human whole blood using a Fluorescent Activated Cell Sorter (FACS) instrument. The FACS uses laser excitation to detect leukocytes by measuring the autofluorescence of leukocyte DNA. The assay of Example 3 provides a method of detecting the three main classes of leukocytes (i.e., granulocytes, lymphocytes, and monocytes) using forward scatter (FSC) to determine characteristic cell sizes and using side scatter (SCC) to determine characteristic cell granularities.

In response to stimulation by a chemokine and/or M-CSF, the monocyte cell population as measured by FSC (i.e., size) increases. The measured response is indicative of either a cell shape change (e.g., ruffling of cell membrane) and/or a homotypic aggregation of monocyte cells. Both cell shape change and homotypic aggregation of monocyte cells occur during initial activation, adhesion, and transendothelial migration of chemokine-activated monocytes.

In the assay, a volume (90 μL) of human whole blood was combined with an aqueous solution (10 μL) containing a known concentration of M-CSF (or optionally M-CSF and MCP-1 if direct measurement of the inhibition of the synergistic effect of M-CSF.on MCP-1 induced chemotaxis is desired), and the mixture was incubated at 37° C. for 30 minutes. A 0.5% solution of formalin (100 μL) was added, and the cells were fixed for 5 minutes. Red blood cell lysis was then achieved by adding 1 mL of lysis buffer and incubating the mixture at 37° C. for 5 minutes. An aliquot of the mixture was then withdrawn, and its monocyte population analyzed using FACS.

The method of the present invention which is the assay of Example 3 provides a number of advantages over traditional methods of studying monocytes. First, the assay is substantial easier to use than current methods as isolation of monocytes from whole blood is no longer necessary. Second, the assay provides a method for analyzing monocytes in their normal environment of serum, other blood cell types, serum esterase, and potential protein binding whereas certain literature methods assay monocytes in isolated peripheral blood mononuclear cells (PBMCs). Third, isolation of PBMCs ages and activates the monocytes whereas the present assay does not so activate the monocytes. Fourth, the assay of Example 3 allows monocytes to be directly used as a surrogate marker for an inflammatory or atherosclerotic condition in in vivo animal and human efficacy studies.

In a procedure analogous to that described above in Example 2, antagonists of an M-CSF receptor may be identified as described below in Example 4.

EXAMPLE 4

This assay utilizes the binding properties of M-CSF to a soluble M-CSF receptor. The assay may be employed to screen single compounds or used in high throughput screening mode to screen many compounds rapidly.

1. Obtain soluble M-CSF receptor from R&D Systems Inc., Minneapolis, Minn.
2. Biotinylate the soluble M-CSFR from Step 1.
3. Using radiolabeled M-CSF, the expression of this biotinylated, soluble M-CSFR can be quantitated and the binding of M-CSF can be measured.

The binding is performed using radiolabeled ($I^{125}$) M-CSF. Preincubate the biotinylated, soluble M-CSFR from Step 2 in a tube or multi-well plate for 30 minutes. Add ($I^{125}$)-M-CSF, and incubate for 2 hours in the presence or absence of cold (i.e., not radiolabeled) M-CSF. Pass the mixture through streptavidin-coated scintillation beads to bind the biotinylated, soluble M-CSFR. The amount of incorporated radioactive material is measured using a scintillation counter. The amount of scintillation count is proportional to the amount of bound radiolabeled M-CSF, and a high ratio of radiolabeled M-CSF (to radiolabeled M-CSF plus non-radiolabeled M-CSF) binding indicates less non-specific binding.

4. To screen for M-CSFR antagonists, preincubate the biotinylated, soluble M-CSFR from Step 2 with a compound or compounds of the present invention (or for that matter any compound(s) for which it is desired to measure inhibition of M-CSF) for 30 minutes, at which point, the radiolabeled M-CSF is added, and incubation is continued for 2 hours more. An antagonist will decrease the binding of the M-CSF to its receptor, and this decrease will be evident from the decreased binding of radiolabeled M-CSF on the cells.
5. The effective concentrations of the antagonists will be evaluated by performing a dose-response curve on the inhibitors of the present invention. An antagonist might represent a molecule that binds to the receptor and dose not allow the receptor's ligand to bind, or it could be a compound that binds to the receptor's ligand and dose not let the ligand bind to the receptor.

Similar protocols can be developed to screen for M-CSF antagonists using kinase assay systems or gene transcriptional activation systems using reporter constructs. All of these protocols are amenable for high throughput screening.

DETAILED DESCRIPTION OF THE DRAWINGS

As shown above, several experiments were conducted to confirm that G-CSF synergizes the IL-8 induced chemotaxis in vivo and in vitro. The methods and materials employed to conduct the studies are discussed in detail above in Example 1, which serves to guide those skilled in the art in understanding the inventions described herein. The results are summarized in FIGS. 1 through 13. The synergy of G-CSF on IL-8 chemotaxis is demonstrated in FIG. 1 where increases in G-CSF concentration, on a picomolar level, increases the chemotactic response of neutrophils. Similarly, the synergy of GM-CSF on IL-8 chemotaxis is demonstrated in FIG. 2. FIG. 3 illustrates the dose response curve for IL-8 with fixed G-CSF concentration and demonstrates a 10-fold increase in neutrophil response to a combination of IL-8 and G-CSF. FIG. 4 shows that G-CSF does not synergize the f-MLP induced neutrophil chemotaxis, indicating an IL-8, and chemokines functionally and/or structurally similar to IL-8, specific phenomenon. FIG. 5 shows that the synergy is not limited to in vitro studies, but is also shows that G-CSF enhances in vivo neutrophil intradermal recruitment. FIG. 6 illustrates and confirms the binding of $I^{125}$ G-CSF to neutrophils. FIG. 7 illustrates that G-CSF neutralizing antibody inhibits G-CSF synergized chemotaxis. FIG. 8 illustrates that G-CSF preincubation alters PMN chemotactic response to IL-8. FIGS. 9 and 10 demonstrate that G-CSF synergism is independent of its effects on IL-8 binding or IL-8 induced calcium flux, suggesting involvement of a signaling mechanism. The study was conducted by employing radiolabeled $I^{125}$ G-CSF and studying its effects on polymorpho nuclear neutrophils (PMN). FIG. 11 illustrates that G-CSF preincubation does not alter IL-8 binding. FIG. 12 illustrates that G-CSF pre-incubation alters PMN response to IL-8. FIG. 13 illustrates that the potentiation effects of G-CSF on IL-8 induced migration were approximately equal on both the chemotactic and chemokinetic responses. The enhancement of IL-8 induced migration was evident irrespective of whether G-CSF was placed in the top or bottom of the chemotaxis chamber.

In summary, the data illustrated in FIGS. 1 through 13 show that G-CSF at biologically relevant concentrations (10–1000 pM) significantly potentiates IL-8 specific chemotaxis, but G-CSF does not affect f-MLP induced chemotaxis. Further, the data show that these acute effects of G-CSF are not mediated via effects on IL-8 binding or IL-8-induced calcium flux. However, the data also show that preincubation of neutrophils, in vitro with G-CSF for 120 minutes desensitized the neutrophils for subsequent IL-8 activation.

Several experiments were conducted that demonstrate M-CSF synergized MCP-1 induced chemotaxis. The methods and materials employed to conduct the studies are described above in Example 3. The results are illustrated in FIGS. 14 through 21. In FIG. 14, a FACS dot plot of FSC versus SSC on unstimulated human whole blood shows that the three main classes of leukocytes can be detected, with normal monocytes plotted in the quadrant labeled R1 and monocytes with greater FSC (i.e., size) plotted in the quadrant labeled R2. The effect of MCP-1 stimulation on monocyte size is shown in FIG. 15, where stimulation by MCP-1 increases the number of monocytes with greater FSC (i.e., size). The effect on FSC as a percent of a control value over time in response to stimulation of monocytes by MCP-1 at a concentration of 50 nM is shown in FIG. 16 to increase until a plateau is reached nearly 30 minutes after initial exposure. In FIG. 17, a dose response curve illustrates that monocyte size, as measured by FSC as a percent of a control value, increases with increasing doses of MCP-1 until a peak is reached at about 100 nM of MCP-1. The $EC_{50}$ in this experiment was 2 nM of MCP-1. FIG. 18 illustrates that an antibody to the chemokine receptor for MCP-1, i.e., an antibody to the CCR-2 receptor, inhibits MCP-1 stimulation of monocytes as shown by the dose response curves of monocyte size, as measured by FSC as a percent of a control value, versus concentration of MCP-1. As expected, the shift of the MCP-1 plus antibody curve is parallel to the MCP-1 alone curve, which demonstrates that the observed effect is MCP-1 dependent and not due to a contaminant such as an endotoxin. In FIG. 19, a dose response curve illustrates that monocyte size, as measured by FSC as a percent of a control value, increases with increasing doses of M-CSF, with an $EC_{50}$ for M-CSF of 253 pM. M-CSF is shown in FIG. 20 to have no effect on the shape of human neutrophils. FIG. 21 illustrates the synergistic effect of M-CSF on MCP-1 induced change in human monocyte shape, as the number of "large" monocytes in the presence or absence of M-CSF versus change in MCP-1 concentration. At a concentration of 1 pM of M-CSF, no statistically significant change in the dose response curve of MCP-1 was observed. However, at concentrations of 10 pM and 100 pM of M-CSF, the dose response curves were shifted towards lower concentrations of MCP-1 (i.e., to the left) by about 1 to 2 log units (i.e., by a factor of 0.1 to 0.01), and the overall response of monocytes to MCP-1 was significantly increased.

In summary, the data illustrated in FIGS. 14 through 21 show that MCP-1 directly acts on monocytes in human whole blood in a time- and concentration-dependent manner. M-CSF alone much more potently induces changes in the shape of monocytes as compared to its effect on changes in the shape of neutrophils. M-CSF synergistically increases the potency of MCP-1 induced effects on monocytes from an $EC_{50}$ of 2 nM to and $EC_{50}$ of 20 pM. In vivo, picomolar concentrations of M-CSF and nanomolar concentrations of MCP-1 are found. The synergistic effects described above for M-CSF and MCP-1 are biologically significant, and inhibitors of the synergistic effect of M-CSF on a chemokine such as, for example, MCP-1 involved in monocyte-mediated inflammation, osteoporosis, an autoimmune disease, or atherosclerosis would be valuable therapeutic agents for the treatment thereof.

The dose and dosage regiment of an inhibitor of the present invention that is suitable for administration to a particular patient can be determined by a physician considering the patient's age, sex, weight, general medical condition, and the specific condition and severity thereof for which the inhibitor of the present invention is being administered; the route of administration of the inhibitor; the pharmaceutical carrier with which the inhibitor may be combined; and the inhibitor's biological activity.

Generally, intravenous subcutaneous or transmuscular injection of 1–500 μMol of CSF antagonizing compounds/kg body weight, by bolus injection, by infusion over a period of about 5 minutes to about 60 minutes, or by continuous infusion is sufficient for therapeutic efficacy. Aerosol inhalation of 0.1 to 2 mg of an inhibitor of the present invention/kg body weight is also sufficient for efficacy.

Intravenous, subcutaneous or intramuscular administration, by bolus injection or continuous infusion, is preferred for use of some of the inhibitors of the present invention in treatment of autoimmune or inflammatory disease.

The inhibitors of the present invention, or a pharmaceutically acceptable salt thereof, can be combined, over a wide concentration range (e.g., 0.001 to 11.0 wt %) with any standard pharmaceutical carrier (e.g., physiological saline, THAM solution, or the like) to facilitate administration by any of various routes including intravenous, subcutaneous, intramuscular, oral, or intranasal, including by inhalation.

The inhibitors of the present invention can be prepared and administered in a wide variety of oral and parenteral dosage forms. Thus, the inhibitors of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the inhibitors of the present invention can be administered transdermally. The following dosage forms may comprise as the active component an inhibitor of the present invention, or a pharmaceutically acceptable salt thereof.

For preparing pharmaceutical compositions from the inhibitors of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active component with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg, preferably 0.5 mg to 100 mg, according to the particular application and the potency of the active component. The composition can, if desired, also contain other compatible therapeutic agents.

In therapeutic use as antagonists or as agents for the treatment of diseases; the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

Examples of pharmaceutical preparations of the inhibitors of the present invention is described below. Such preparations can be administered to a human from one to six times a day for treatment of disease caused by a synergistic effect of a CSF on chemokine-mediated inflammation, osteoporosis, an autoimmune disease, or atherosclerosis.

EXAMPLE 4

| Tablet Formulation: | |
|---|---|
| Ingredients | Amount (mg) |
| Inhibitor of the invention | 25 |
| Lactose | 50 |
| Cornstarch (for mix) | 10 |
| Cornstarch (paste) | 10 |
| Magnesium stearate (1%) | 5 |
| Total | 100 |

The inhibitor of the present invention, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the I% magnesium stearate and pressed into a tablet.

EXAMPLE 5

Coated Tablets:
The tablets of Example 17 are coated in a customary manner with a coating of sucrose, potato starch, talc, tragacanth, and colorant.

EXAMPLE 6

Injection Vials:
The pH of a solution of 500 g of an inhibitor of the present invention and 5 g of disodium hydrogen phosphate is adjusted to pH 6.5 in 3 L of double-distilled water using 2 M hydrochloric acid. The solution is sterile-filtered, and the filtrate is filled into injection vials, lyophilized under sterile conditions, and aseptically sealed. Each injection vial contains 25 mg of an inhibitor of the present invention.

EXAMPLE 7

Suppositories:
A mixture of 25 g of an inhibitor of the present invention, 100 g of soya lecithin, and 1400 g of cocoa butter is fused, poured into molds, and allowed to cool. Each suppository contains 25 mg of an inhibitor of the present invention.

EXAMPLE 8

Solution:
A solution is prepared from 1 g of the an inhibitor of the present invention, 9.38 g of $NaH_2PO_4.2H_2O$, 28.48 g of Na$_2$HPO$_4$.12H$_2$O, and 0.1 g benzalkonium chloride in 940 mL of double-distilled water. The pH of the solution is adjusted to pH 6.8 using 2 M hydrochloric acid. The solution is diluted to 1.0 L with double-distilled water and sterilized by irradiation. A 25-mL volume of the solution contains 25 mg of an inhibitor of the present invention.

EXAMPLE 9

Ointment:

Five hundred milligrams of an inhibitor of the present invention is mixed with 99.5 g of petroleum jelly under aseptic conditions. A 5-g portion of the ointment contains 25 mg of an inhibitor of the present invention.

EXAMPLE 10

Capsules:

Two kilograms of an inhibitor of the present invention are filled into hard gelatin capsules in a customary manner such that each capsule contains 25 mg of an inhibitor of the present invention.

EXAMPLE 11

Ampoules:

A solution of 2.5 kg of an inhibitor of the present invention is dissolved in 60 L of double-distilled water. The solution is sterile-filtered, and the filtrate is filled into ampoules. The ampoules are lyophilized under sterile conditions and aseptically sealed. Each ampoule contains 25 mg of an inhibitor of the present invention.

The embodiments of the present invention described above are hereupon claimed.

What is claimed is:

1. A method of treating rheumatoid arthritis in a mammal comprising administering to said mammal a therapeutically effective amount of an antibody to a M-CSF that is effective to treat said rheumatoid arthritis.

2. The method of claim 1 wherein said antibody is a monoclonal antibody.

3. The method of claim 1, wherein said M-CSF is a human M-CSF.

4. The method of claim 2, wherein said M-CSF is a human M-CSF.

5. A method of treating rheumatoid arthritis in a human comprising administering to said human a therapeutically effective amount of a monoclonal antibody to a human M-CSF that is effective to treat said rheumatoid arthritis.

6. A method of treating rheumatoid arthritis in a human comprising administering to said human a therapeutically effective amount of a monoclonal antibody to a M-CSF.

7. A method of treating rheumatoid arthritis in a human comprising administering to said human a therapeutically effective amount of a monoclonal human antibody to a human M-CSF.

* * * * *